US011229389B2

(12) United States Patent
Shinohara

(10) Patent No.: US 11,229,389 B2
(45) Date of Patent: Jan. 25, 2022

(54) INFORMATION PROCESSING DEVICE, BIOMEDICAL-SIGNAL MEASURING SYSTEM, AND RECORDING MEDIUM STORING PROGRAM CODE

(71) Applicant: Ricoh Company, Ltd., Tokyo (JP)

(72) Inventor: Michinari Shinohara, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 402 days.

(21) Appl. No.: 16/161,164

(22) Filed: Oct. 16, 2018

(65) Prior Publication Data
US 2019/0200887 A1 Jul. 4, 2019

(30) Foreign Application Priority Data
Dec. 28, 2017 (JP) .............................. JP2017-254770

(51) Int. Cl.
*A61B 5/00* (2006.01)
*A61B 5/245* (2021.01)
*G16H 30/40* (2018.01)
*A61B 5/291* (2021.01)
*G01R 33/02* (2006.01)
(Continued)

(52) U.S. Cl.
CPC .............. *A61B 5/245* (2021.01); *A61B 5/291* (2021.01); *A61B 5/743* (2013.01); *G16H 30/40* (2018.01); *A61B 5/7425* (2013.01); *G01R 33/02* (2013.01); *G06F 40/169* (2020.01); *G06T 11/60* (2013.01);
(Continued)

(58) Field of Classification Search
CPC ... A61B 5/04008; A61B 5/0478; A61B 5/743; A61B 5/7425; A61B 5/245; A61B 5/291; G16H 30/40; G06F 40/169; G06T 2200/24
See application file for complete search history.

(56) References Cited

U.S. PATENT DOCUMENTS

| 10,679,394 B2 * | 6/2020 | Shinohara ............... G06T 11/60 |
| 2007/0083097 A1 * | 4/2007 | Fujiwara ............ A61B 5/14553 600/407 |

(Continued)

FOREIGN PATENT DOCUMENTS

| JP | 2009-118910 | 6/2009 |
| JP | 2009-169545 | 7/2009 |

(Continued)

*Primary Examiner* — Shen Shiau
(74) *Attorney, Agent, or Firm* — Xsensus LLP

(57) ABSTRACT

An information processing device, a biomedical-signal measuring system, and a recording medium storing program code for causing a computer to execute a biomedical signal display method. The information processing device includes circuitry to display, on a display device, a first waveform display area indicating a waveform that indicates changes over time in a biomedical signal, and display a distribution display area indicating a distribution of the biomedical signal. Once input data indicating selection of a certain point of the waveform displayed in the first waveform display area is accepted, the circuitry displays the distribution display area based on the input data when the distribution display area is hidden from view, and the circuitry updates the distribution indicated in the distribution display area before the input data is accepted to a distribution based on the input data and displays the updated distribution when the distribution display area is being displayed.

8 Claims, 29 Drawing Sheets

(51) Int. Cl.
*G06T 11/60* (2006.01)
*G06F 40/169* (2020.01)

(52) U.S. Cl.
CPC ...... *G06T 2200/24* (2013.01); *G06T 2210/41* (2013.01)

(56) References Cited

U.S. PATENT DOCUMENTS

| | | | | |
|---|---|---|---|---|
| 2012/0278099 | A1* | 11/2012 | Kelly | G16H 10/60 |
| | | | | 705/3 |
| 2015/0071517 | A1* | 3/2015 | Park | G01R 33/546 |
| | | | | 382/131 |
| 2015/0227702 | A1* | 8/2015 | Krishna | A61B 5/7257 |
| | | | | 705/2 |
| 2015/0248534 | A1* | 9/2015 | Krzywicki | G06F 3/04842 |
| | | | | 715/771 |
| 2018/0268588 | A1* | 9/2018 | Shinohara | G06F 40/169 |
| 2018/0325483 | A1* | 11/2018 | Shinohara | A61B 5/369 |
| 2019/0021676 | A1* | 1/2019 | Shinohara | A61B 5/7435 |
| 2019/0087996 | A1* | 3/2019 | Shinohara | G06T 11/60 |
| 2019/0129606 | A1* | 5/2019 | Shinohara | A61B 5/7445 |
| 2019/0236824 | A1* | 8/2019 | Shinohara | G06T 11/60 |
| 2019/0274640 | A1* | 9/2019 | Mukasa | A61B 5/7435 |
| 2019/0282111 | A1* | 9/2019 | Yamagata | A61B 5/04008 |
| 2019/0282174 | A1* | 9/2019 | Yamagata | A61B 5/7285 |
| 2019/0282176 | A1* | 9/2019 | Yamagata | A61B 5/7425 |
| 2019/0282181 | A1* | 9/2019 | Yamagata | A61B 5/369 |
| 2020/0289006 | A1* | 9/2020 | Yamagata | A61B 5/0042 |
| 2020/0294189 | A1* | 9/2020 | Yamagata | G06T 3/0093 |
| 2020/0294296 | A1* | 9/2020 | Yamagata | A61B 5/743 |
| 2020/0297231 | A1* | 9/2020 | Yamagata | A61B 5/7475 |

FOREIGN PATENT DOCUMENTS

| | | |
|---|---|---|
| JP | 2010-094358 | 4/2010 |
| JP | 2016-202382 | 12/2016 |
| JP | 2018-089336 | 6/2018 |

* cited by examiner

FIG. 10

INFORMATION PROCESSING DEVICE, BIOMEDICAL-SIGNAL MEASURING SYSTEM, AND RECORDING MEDIUM STORING PROGRAM CODE

CROSS-REFERENCE TO RELATED APPLICATION

This patent application is based on and claims priority pursuant to 35 U.S.C. § 119(a) to Japanese Patent Application No. 2017-254770, filed on Dec. 28, 2017, in the Japan Patent Office, the entire disclosure of which is hereby incorporated by reference herein.

BACKGROUND

Technical Field

Embodiments of the present disclosure relate to an information processing device, a biomedical-signal measuring system, and a recording medium storing program code for causing a computer to execute a biomedical signal display method.

Background Art

Current non-invasive methods of recording the activity of the neurons of the brain include a method of detecting the electrical activity of nerve cells of the brain with an electroencephalograph and a method of detecting the magnetic field generated by the brain caused by the brain's electrical activity with a magneto-encephalograph. Analysts control a display to display the data detected by these methods as waveforms, and estimate the signal source based on, for example, the amplitude of such waveforms and the current distribution inside a live subject.

Moreover, information processing devices are known in the art that display multiple types of image data within a single window screen (display area). Such information processing devices are used by analysts after the magnetic field is measured to analyze the obtained measurement data and prepare documental data such as a report.

SUMMARY

Embodiments of the present disclosure described herein provide an information processing device, a biomedical-signal measuring system, and a recording medium storing program code for causing a computer to execute a biomedical signal display method. The information processing device includes circuitry to display, on a display device, a first waveform display area indicating a waveform that indicates changes over time in a biomedical signal, and display a distribution display area indicating a distribution of the biomedical signal. Once input data indicating selection of a certain point of the waveform displayed in the first waveform display area is accepted, the circuitry displays the distribution display area based on the input data when the distribution display area is hidden from view, and the circuitry updates the distribution indicated in the distribution display area before the input data is accepted to a distribution based on the input data and displays the updated distribution when the distribution display area is being displayed. The biomedical-signal measuring system includes a measurement device to measure at least one biomedical signal of a test subject, a server to store the at least one biomedical signal measured by the measurement device, and the information processing device. The biomedical signal display method includes displaying, on a first waveform display area, a waveform that indicates changes over time in a biomedical signal, accepting input data indicating a certain point of the waveform selected in the first waveform display area, displaying a distribution display area based on the input data when the distribution display area is hidden from view; and updating the distribution indicated in the distribution display area before the input data is accepted to a distribution based on the input data and displaying the updated distribution when the distribution display area is being displayed.

BRIEF DESCRIPTION OF THE DRAWINGS

A more complete appreciation of exemplary embodiments and the many attendant advantages thereof will be readily obtained as the same becomes better understood by reference to the following detailed description when considered in connection with the accompanying drawings.

FIG. 10 is a diagram illustrating a screen displayed when magneto-encephalogram distribution maps and a brain-wave distribution map are closed on the screen of FIG. 7.

Figure 1:
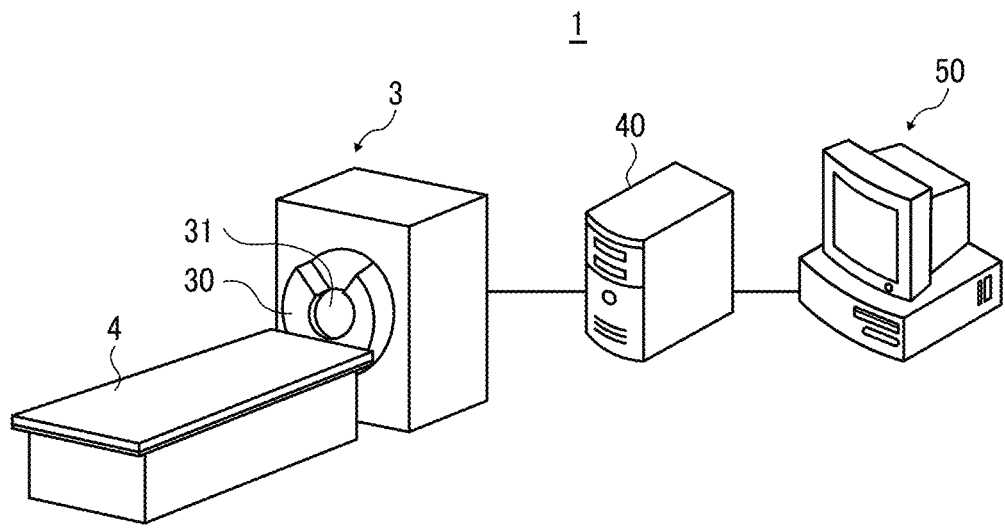
FIG. 1 is schematic diagram illustrating a biomedical-signal measuring system according to an embodiment of the present disclosure.

The accompanying drawings are intended to depict exemplary embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the waits "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments shown in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

In the following description, illustrative embodiments will be described with reference to acts and symbolic representations of operations (e.g., in the form of flowcharts) that may be implemented as program modules or functional processes including routines, programs, objects, components, data structures, etc., that perform particular tasks or implement particular abstract data types and may be implemented using existing hardware at existing network elements or control nodes. Such existing hardware may include one or more central processing units (CPUs), digital signal processors (DSPs), application-specific-integrated-circuits (ASICs), field programmable gate arrays (FPGAs), computers or the like. These terms in general may be collectively referred to as processors.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

With reference to the drawings, an information processing device, a biomedical-signal measuring system, and a recording medium storing a program according to an embodiment of the present disclosure will be described below in detail.

FIG. 1 is schematic diagram illustrating a biomedical-signal measuring system 1 according to an embodiment of the present disclosure. The biomedical-signal measuring system 1 measures various kinds of biomedical signals of a test subject (person to be measured) such as magneto-encephalography (MEG) signals and electro-encephalography (EEG) signals, and displays the results of measurement. The biomedical signals to be measured are not limited to the magneto-encephalography (MEG) signals and electro-encephalography (EEG) signals as above, but may be, for example, any electrical signal that is caused by cardiac activity (i.e., any electrical signal that can be expressed in an electrocardiogram (ECG)). As illustrated in FIG. 1, the biomedical-signal measuring system 1 includes a measurement device 3 that measures at least one biomedical signal of a test subject, a server 40 that stores at least one biomedical signal measured by the measurement device 3, and an information processing device 50 that analyzes at least one biomedical signal stored on the server 40. In the present embodiment, the server 40 and the information processing device 50 are described as separate units. However, no limitation is indicated thereby. For example, at least some of the functions of the server 40 may be implemented by the information processing device 50.

In the present embodiment as illustrated in FIG. 1, a test subject lies on a measurement table 4 on his or her back with electrodes (or sensors) attached to his or her head to measure the electrical brain waves, and puts his or her head into a hollow 31 of a Dewar 30 of the measurement device 3. The Dewar 30 is a container of liquid helium that can be used at very low temperatures, and a number of magnetic sensors for measuring the brain magnetism are disposed on the inner surface of the hollow 31 of the Dewar 30. Note that such magnetic sensors for measuring the brain magnetism may be referred to simply as sensors. The measurement device 3 collects the electrical signals and the magnetic signals through the electrodes and the magnetic sensors, respectively, and outputs data including the collected electrical signals and magnetic signals to the server 40. Note that such collected electrical signals and magnetic signals may be referred to simply as "measurement data" in the following description of the present embodiment. The measurement data recorded on the server 40 is read and displayed by the information processing device 50, and is analyzed by the information processing device 50. As known in the art, the Dewar 30 integrated with magnetic sensors and the measurement table 4 is inside a magnetically shielded room. However, for the sake of explanatory convenience, such a magnetically shielded room is omitted in FIG. 1.

The information processing device 50 synchronizes and displays the waveform of the magnetic signals obtained through the multiple magnetic sensors and the waveform of the electrical signals obtained through the multiple electrodes on the same time axis. The brain-wave signals indicate the inter-electrode voltage value obtained for the electrical activity of nerve cells (i.e., the flow of ionic charge caused at the dendrites of neurons during synaptic transmission). Moreover, the magnetic signals (brain-magnetism signals) indicate minute changes in magnetic field caused by the electrical activity of the brain. The magnetic field of the brain is detected by a high-sensitivity superconducting quantum interference device (SQUID). These electrical signals and magnetic signals are examples of biomedical signals.

Figure 2:
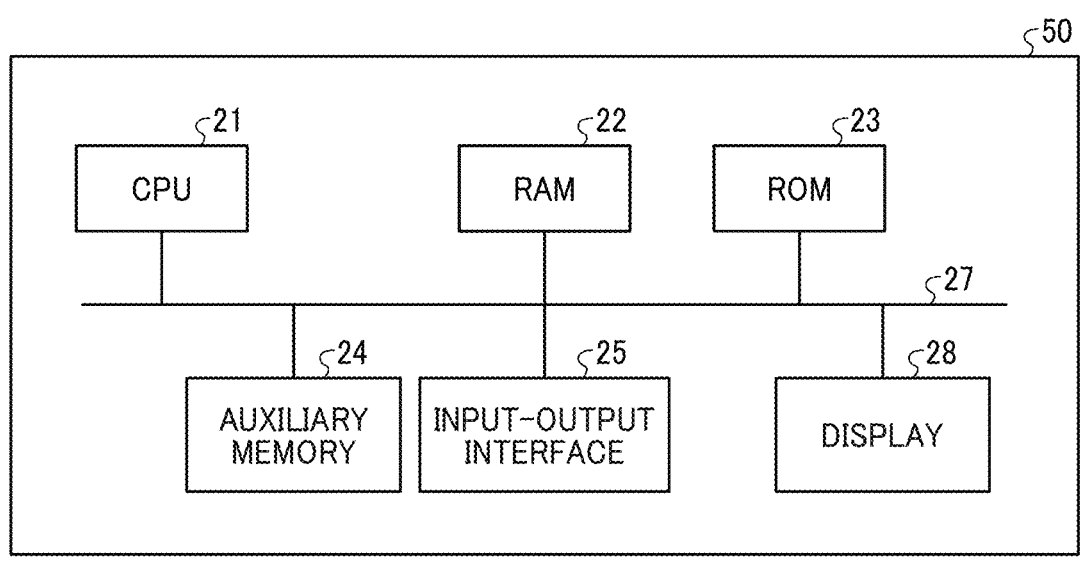
FIG. 2 is a block diagram illustrating a hardware configuration of an information processing device according to an embodiment of the present disclosure.

FIG. 2 is a schematic block diagram illustrating a hardware configuration of the information processing device 50, according to the present embodiment. The information processing device 50 is provided with a central processing unit (CPU, processor) 21, a random access memory (RAM) 22, a read only memory (ROM) 23, an auxiliary storage device 24, an input-output interface 25, and a display 28, and these elements are interconnected through a bus 27.

The CPU 21 controls the entire operation of the information processing device 50, and performs various kinds of information processing. Moreover, the CPU 21 executes an information displaying program stored in the ROM 23 or the auxiliary storage device 24, to control the display of the measurement and recording screen and the analyzing screen. The RAM 22 is used as a work area of the CPU 21, and may include a nonvolatile RAM in which a desired control parameter or desired data are stored. For example, the ROM 23 stores a basic input and output program. The ROM 23 may also store the information displaying program according to the present embodiment. The auxiliary storage device 24 is a storage device such as a solid state disk (SSD) and a hard disk drive (HDD), and stores, for example, a control program to control the operation of the information processing device 50, various kinds of data used to operate the information processing device 50, and files. The input-output interface 25 is provided with both a user interface such as a touch panel, a keyboard, a display screen, and an operation key and a communication interface that takes in data from various kinds of sensors or the server 40 and outputs the analyzed data to another external electronic device. The display 28 is a device for displaying various kinds of information thereon. The measurement and recording screen and the analyzing screen are displayed on the display 28, and the screen of the display 28 is updated in response to input and output operation through the input-output interface 25.

Figure 3:
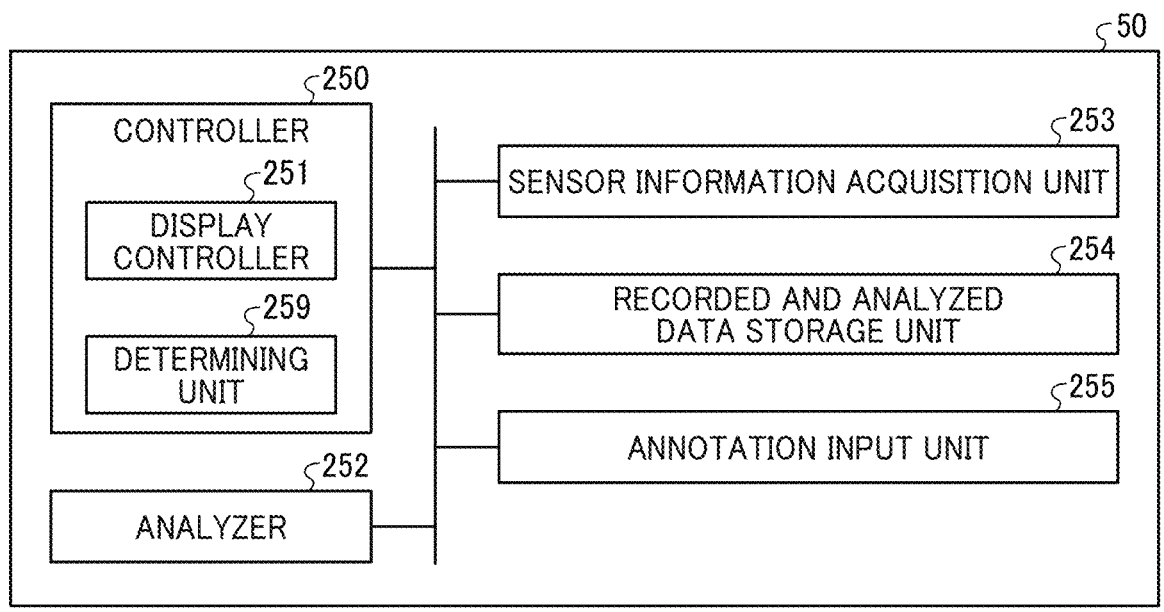
FIG. 3 is a functional block diagram of an information processing device according to an embodiment of the present disclosure.

FIG. 3 is a functional block diagram of the information processing device 50 according to the present embodiment. The information processing device 50 includes a controller 250, an analyzer 252, a sensor information acquisition unit 253, a recorded and analyzed data storage unit 254, and an annotation input unit 255. The controller 250 includes a determining unit 259 that makes various kinds of determinations and a display controller 251 that controls the visual display of the information processing device 50.

The sensor information acquisition unit 253 obtains sensor information from the measurement device 3 or the server 40. The annotation input unit 255 inputs annotation data to be added to the sensor information. The analyzer 252 analyzes the collected sensor information. The analysis of sensor information includes signal waveform analysis, analysis of singular point of amplitude, and analysis of magnetic field of the brain including the direction of a current dipole. In other words, in the present embodiment, the analyzer 252 serves as an estimation unit and functions to estimate a signal source that corresponds to the annotation selected on the analyzing screen. The display controller 251 controls the visual display when the sensor information is measured and recorded or analyzed, according to the above-described method. The recorded and analyzed data storage unit 254 stores the measurement data and the analytical results. When an annotation is added to the signal waveform during the measurement and recording, the added annotation is also stored in association with the time at which the signal waveform is obtained. The functions of the controller 250 including the display controller 251 may be implemented as the CPU 21 illustrated in FIG. 2 launches a program stored in a memory such as the ROM 23 onto the RAM 22 and executes the launched program. The functions of the analyzer 252 may also be implemented as the CPU 21 launches a program stored in a memory such as the ROM 23 onto the RAM 22 and executes the launched program. However, no limitation is intended thereby. For example, at least some of these functions of the controller 250 and the analyzer 252 may be implemented by a dedicated hardware circuit such as a semiconductor integrated circuit. The functions of the sensor information acquisition unit 253 and the annotation input unit 255 are implemented by the input-output interface 25. The functions of the recorded and analyzed data storage unit 254 are implemented by the ROM 23 or the auxiliary storage device 24.

Figure 4:
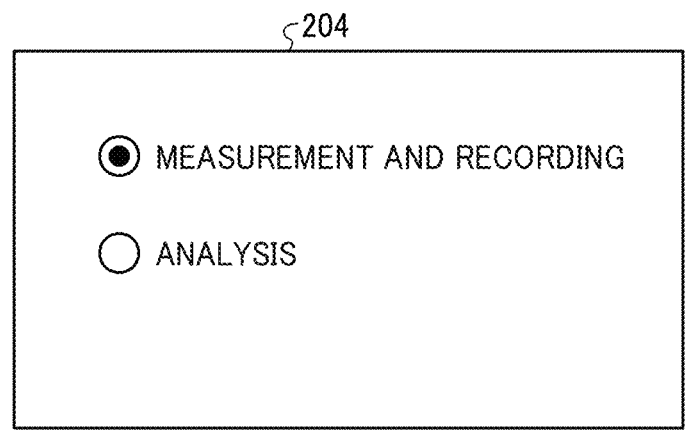
FIG. 4 is a diagram illustrating a starting screen displayed on an information processing device, according to an embodiment of the present disclosure.

FIG. 4 is a diagram illustrating a starting screen 204 displayed on the information processing device 50, according to the present embodiment. On the starting screen 204, selection boxes "measurement and recording" and "analysis" are displayed. When the brain wave or brain magnetism is to be measured, in many cases, the person who measures and records the data and the person who analyzes the data are different. For example, when the "measurement and recording" box is selected by a measurement engineer (technician), the data measured by the measurement device 3 is sequentially stored on the server 40, and is read and displayed by the information processing device 50. On the other hand, when the "analysis" box is selected by a doctor after the measurement and recording is done, the recorded measurement data is read and analyzed.

Figure 5:
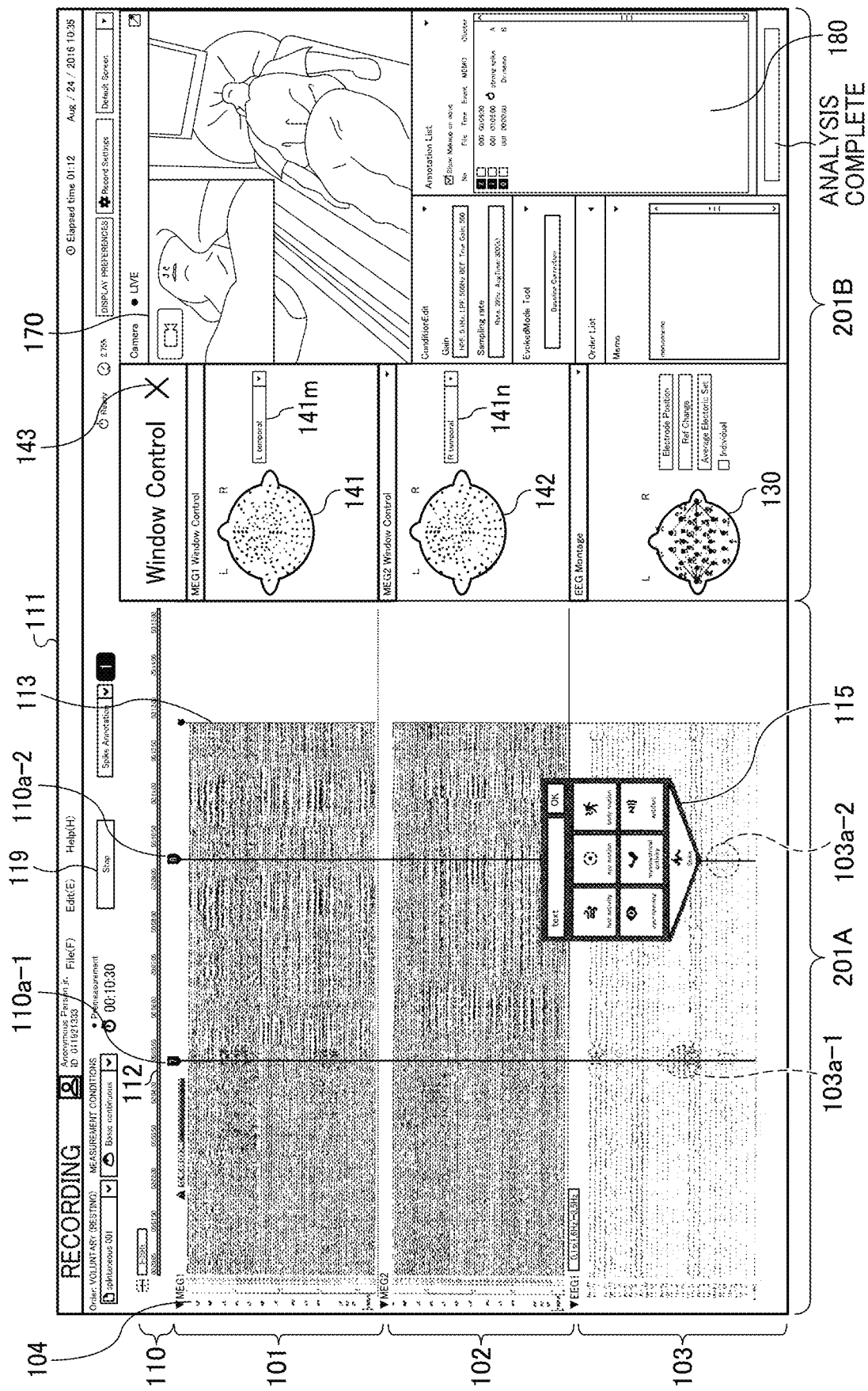
FIG. 5 is a diagram illustrating a measurement and recording screen according to an embodiment of the present disclosure.

FIG. 5 is a diagram illustrating a measurement and recording screen according to the present embodiment. The measurement and recording screen includes an area 201A on which measured signal waveform is displayed, and an area 201B on which monitoring data other than the signal waveform is displayed. The area 201A on which signal waveform is displayed is arranged on the left side of the screen as viewed by the technician, and the area 201B on which monitoring data other than the signal waveform is displayed is arranged on the right side of the screen as viewed by the technician. Accordingly, there is an economy of motion between the movement of the mouse from the area 201A on the left side of the screen to the area 201B on the right side of the screen and the motion of the line of sight of a technician that follows the movement of a waveform (detected in real time and dynamically displayed from the left side of the screen to the right side of the screen), and the efficiency improves.

In the area 201B of the display screen, a monitoring window 170 is displayed to monitor the state of a subject during measurement. By displaying the live image of the subject while he/she is being measured, the reliability of the check and judgment of a signal waveform can be improved.

The area 201A includes a time-indicating area 110 in which the time data of signal detection is displayed in the horizontal direction (i.e., the first direction) of the screen, and waveform display areas 101 to 103 in which a plurality of signal waveforms based on the signal detection are displayed in parallel in the vertical direction (i.e., the second direction) of the screen.

The time data that is displayed in the time-indicating area 110 is a time line including the time indication given along a time axis 112. However, no limitation is indicated thereby, and such a time line may only be a band-like or belt-like axis where no time (time in number) is displayed, or may only be the time (time in number) where no axis is given. Alternatively, a time line may be displayed by displaying a time axis under the waveform display area 103 in addition to time-indicating area 110 on the topside of the screen.

In the area 201A, a plurality of signal waveforms obtained by a plurality of similar kinds of sensors or various kinds of signal waveforms obtained by a group of a plurality of different kinds of sensors are displayed in a synchronous manner along the same time axis. For example, the waveforms of a plurality of magneto-encephalography (MEG) signals obtained from the right side of the head of a subject and the waveforms of a plurality of magneto-encephalography (MEG) signals obtained from the left side of the head of a subject are displayed parallel to each other in the waveform display area 101 and the waveform display area 102, respectively. In the waveform display area 103, the waveforms of a plurality of electro-encephalography (EEG) signals are displayed in parallel. These waveforms of a plurality of electro-encephalography (EEG) signals correspond to the voltage signals measured between pairs of electrodes. Each of these waveforms of a plurality of signals is displayed along a channel axis 104 in association with the identification number or channel number of the sensor through which the signal is obtained.

Once measurement is started and the readings from each sensor are collected, as time passes a signal waveform is displayed moving from left to right in each of the waveform display areas 101 to 103 in the area 201A. A vertical line 113 indicates the measurement time (present time), and moves from the left side to the right side of the screen. Once the signal waveform display reaches the right end of the area 201A (i.e., until the right end of the time axis 112), the signal waveform gradually disappears from the left end of the screen to the right. Then, new signal waveforms are displayed at disappearing positions in sequence from the left side to the right side, and the line 113 also moves from the left end of the screen to the right. Together with the above changes on the display, the lapse of time is also displayed in the horizontal time-indicating area 110 along the time axis 112 as the measurement progresses. The measurement and recording continues until the stop key 119 is touched or clicked.

In the present embodiment, when the technician (i.e., a person who records the data) notices, for example, irregularities in waveform and a singular point of amplitude on the signal waveform during the data recording, he/she can mark a problematic point or area on the signal waveform. The point or area of such a problematic point or area to be marked can be specified by moving a mouse cursor and clicking with a mouse. The specified point or area is highlighted on the signal waveforms of the waveform display areas 101 to 103, and the specified result is displayed along the time axis 112 of time-indicating area 110 in a relevant point in time or time range. The marking information including the display along the time axis 112 is stored together with the signal waveform data. The specified point corresponds to particular time, and the specified area corresponds to a certain area including the particular time.

In the example illustrated in FIG. 5, an area including at least one channel is specified at a time t1 in the waveform display area 103, and the span of time including the time t1 is highlighted at the mark 103a-1. In association with the display of the mark 103a-1, an annotation 110a-1 that indicates the result of specification is displayed at the corresponding point in time in the time-indicating area 110. At a time t2, another point in waveform or an area around that point is marked in the waveform display area 103, and a mark 103a-2 is highlighted at that point (the time t2) or in the area around that point (the time t2) (where at least one of a time range or a plurality of waveforms is indicated). At the same time, an annotation 110a-2 is displayed at the corresponding point in time (time range) in the time-indicating area 110. Note that the term "annotation" means that related information is given to certain data as an annotation. An annotation according to the present embodiment is displayed at least based on the specified time data in association with the position at which the waveform is displayed based on the time data. When a plurality of channels is displayed, the annotation according to the present embodiment may be displayed in association with the corresponding channel information.

Once the technician specifies another point in waveform or an area around that point in waveform at the time t2, the mark 103a-2 is highlighted at the specified point, and an annotation number "2" is displayed at the corresponding point in time in the time-indicating area 110. Further, a pop-up window 115 for selecting the attribute is displayed at the highlighted point. The pop-up window 115 includes selection keys (buttons) for selecting the various kinds of attribute, and an input box through which a comment or additional information is input. On the selection keys, the causes of irregularities in waveform such as fast activity, eye motion, body motion, and spike are indicated as the attributes of waveform. As the technician can check the state of the subject through the monitoring window 170 of the area 201B in the screen, he/she can select the appropriate attribute indicating the causes of the irregularities in the waveform. For example, when a spike occurs in a waveform, the technician can determine whether such a spike is a symptom of epilepsy or is caused by some other body motion (such as a sneeze) of the subject.

Some of or all of the annotation 110a-1, for example, at least one of an attribute icon and a text annotation, may be displayed near the mark 103a-1 on the signal waveforms in the waveform display area 103. When such an annotation is added directly over the signal waveforms, the ability to check the shape of the waveforms may be impaired. For this reason, when an annotation is displayed over the signal waveforms in the waveform display areas 101 to 103, it is desired that display or non-display of such an annotation be selectable.

In the monitoring window 170 of the area 201B, the live image of the subject lying on the measurement table 4 and the head of the subject inside the measurement device 3 is displayed. In the area 201B, the magneto-encephalogram distribution maps 141 and 142 and the brain-wave distribution map 130, which correspond to the signal waveforms of the waveform display areas 101, 102, and 103, respectively, and the annotation list 180 are displayed.

The magneto-encephalogram distribution maps 141 and 142 indicate the arrangement of the magnetic sensors for measuring brain magnetism. Each of the magnetic sensors is dotted over the magneto-encephalogram distribution maps 141 and 142. The brain-wave distribution map 130 is a brain-wave distribution map that indicates the arrangement of electrodes (or sensors) to measure the brain waves. Preparatory to the measurement and recording, the technician specifies the magnetic sensors that correspond to the waveforms to be displayed on the waveform display areas 101 and 102, on the magneto-encephalogram distribution maps 141 and 142.

For example, the analyst can specify magnetic sensors from the pull-down menu displayed as the menu 141*m* or 141*n* is touched or clicked. For example, the pull-down menu does not only display selection of the right and left groups of sensors, but also displays selectable parts of the brain such as a parietal region, a frontal lobe, and a temporal lobe. When sensors at a parietal region in the magneto-encephalogram distribution map 141 are selected in the menu 141*m*, all the sensors other than sensors at a parietal region in the magneto-encephalogram distribution map 142 are selected in the menu 141*n*. Then, once magnetic sensors are selected, the color of the selected dots on the magneto-encephalogram distribution maps 141 and 142 is changed so as to be visually distinguishable from the unselected dots on the display. The identification numbers or channel numbers of the sensors displayed along the channel axis 104 become the numbers of sensors at a parietal region in the waveform display area 101, and become the numbers of the sensors other than sensors at a parietal region at a parietal region in the waveform display area 102.

As an alternative method for selecting magnetic sensors, the technician or the analyst may use an operation unit such as a mouse to encircle the magnetic sensors (indicated by dots) to be selected on the magneto-encephalogram distribution maps 141 and 142. As a result of this encircling operation, the color of the dots (magnetic sensors) inside the encircled area is changed so as to be distinguishable from the dots outside the encircled area.

The annotation list 180 is a list of annotations marked on the signal waveforms in the area 201A. Every time the point or area on the signal waveforms is specified in the waveform display areas 101 to 103 and an annotation is given, the associated information is sequentially added to the annotation list 180.

When the stop key 119 is selected (touched or clicked) and the measurement is terminated, the highlighted portion specified in the waveform display areas 101 to 103 is stored in association with the signal waveform. The annotation information displayed at the corresponding point in time in the time-indicating area 110 is also stored in association with the annotation number and the time. By storing the above display information, even if the technician and the analyst are different, the analyst can easily recognize and analyze a problematic portion.

Figure 6:
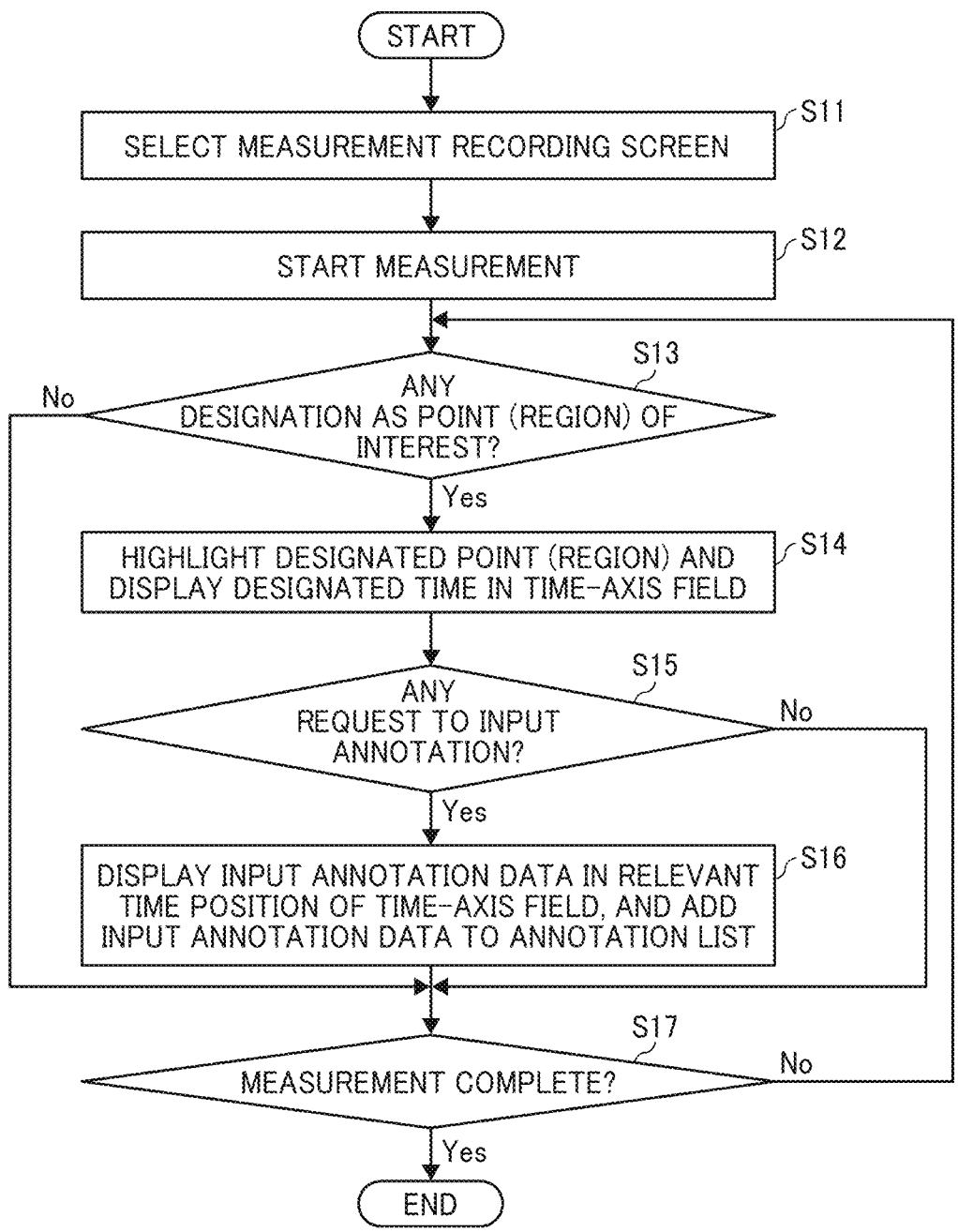
FIG. 6 is a flowchart of the operations performed by an information processing device during the measurement and recording, according to an embodiment of the present disclosure.

FIG. 6 is a flowchart of display information processing performed by the information processing device 50 in a stage of measurement and recording, according to the present embodiment. When "measurement and recording" is selected on the starting screen 204 as illustrated in FIG. 4, the acceptance unit 52 of the information processing device 50 accepts the selection (step S11). Accordingly, the measurement is started, and the display controller 251 controls a display in a synchronous manner along a time axis where the waveforms of a plurality of signals are equivalent to each other (step S12). In the present embodiment, the term "a plurality of signal waveforms" includes both the signal waveform detected by a plurality of sensors of the same kind and the multiple signal waveforms detected by a plurality of various kinds of sensors. In the present embodiment, the waveforms of a plurality of biomedical signals consist of the waveform of the brain-magnetism signals obtained through a plurality of magnetic sensors from the right side of the head of a subject, the waveform of the brain-magnetism signals obtained through a plurality of magnetic sensors from the left side of the head of the subject, and the waveform of the brain-wave signals obtained through electrodes for measuring the electrical brain waves of the subject. However, no limitation is intended thereby.

A determining unit 259 of the information processing device 50 determines whether any designation is made as a point of interest or region of interest in the displayed signal waveform (step S13). When such designation is made [[as a point of interest or a range of interest]] (YES in the step S13), the display controller 251 causes the display to highlight the designated point (region) in the display areas of signal waveform (i.e., the waveform display areas 101 to 103), and display the results of selection in a relevant point in time of the time-axis field (i.e., the time-indicating area 110) (step S14). The result of designation includes data indicating that the designation has been made or the identification information of the designation. The determining unit 259 determines whether or not there is a request to input an annotation at the same time as when the results of selection are displayed in the time-axis field or before or after the results of selection are displayed in the time-axis field (step S15). When there is a request to input an annotation (YES in the step S15), the display controller 251 displays the input annotation data in a relevant point in time of the time-axis field, and adds the input annotation data to the annotation list 180 so as to be displayed therein (step S16). Then, the determining unit 259 determines whether or not a measurement termination command has been input (step S17). On the other hand, when no point of interest or range of interest is designated (NO in the step S13) and when there is no request to input an annotation (NO in the step S15), the process proceeds to a step S17, and the deter wining unit 259 determines that the measurement is completed. Until the measurement is completed (YES in the S17), the processes in the steps S13 to S16 are repeated.

Figure 7:
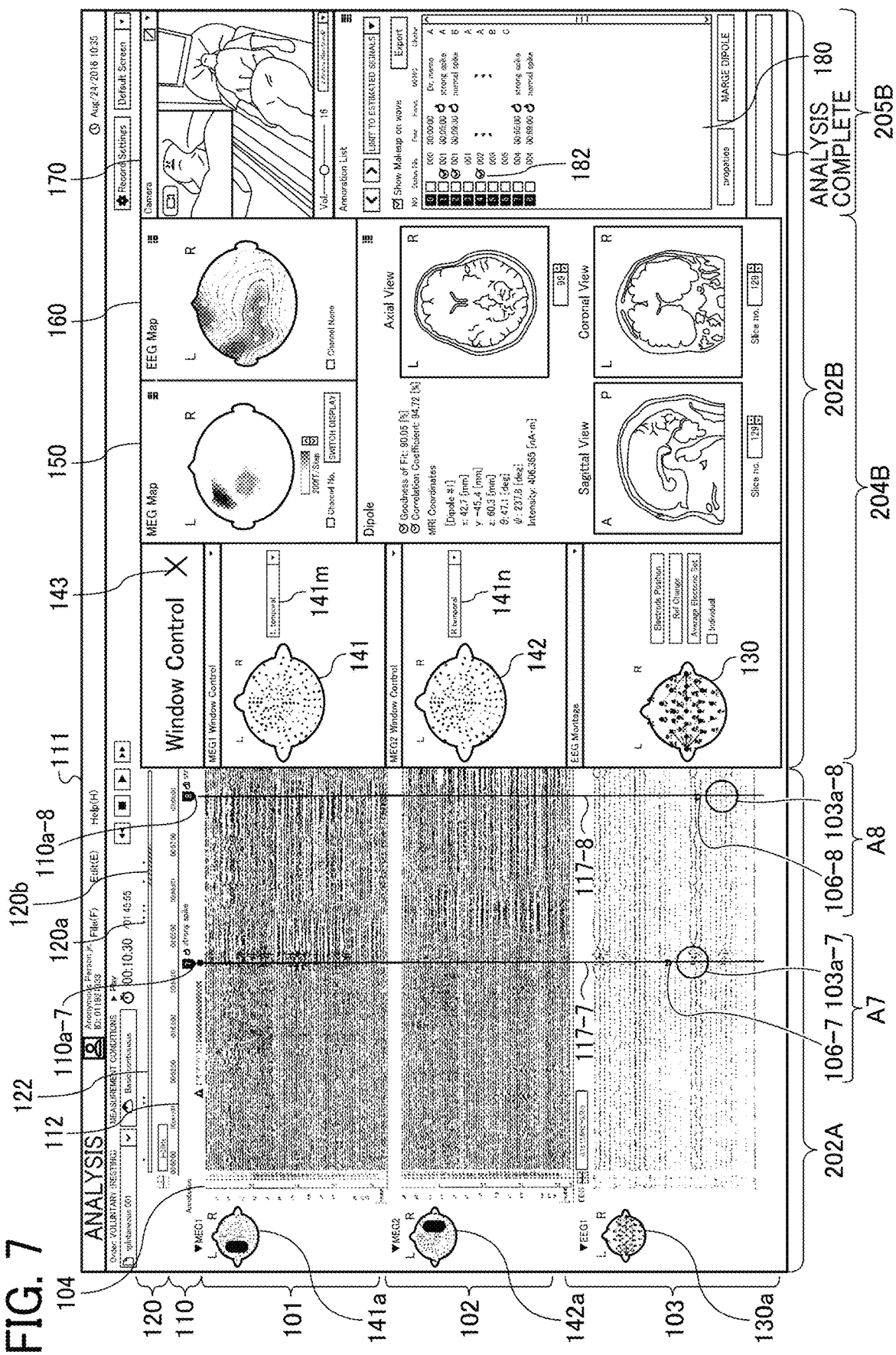
FIG. 7 is a diagram illustrating an analyzing screen according to an embodiment of the present disclosure.

FIG. 7 is a diagram illustrating a screen of the information processing device 50 when analysis is being performed, according to the present embodiment. The analysis screen is displayed as the "analysis" button on the starting screen 204 as illustrated in FIG. 4 is selected. In the analyzing screen, biomedical data that indicates the changes over time in at least one biomedical signal of a test subject obtained in the measurement (i.e., in the present embodiment, the brain-magnetism signals obtained through a plurality of magnetic sensors from the right side of the head of a subject, the brain-magnetism signals obtained through a plurality of magnetic sensors from the left side of the head of a subject, and the brain-wave signals obtained through electrodes for measuring the brain wave of the subject) is associated with at least one annotation that is input and added to the biomedical data during the measurement. In the present embodiment, the display controller 251 of the information processing device 50 controls a display (i.e., a display 28 as will be described later in detail) to display the analyzing screen. In the present embodiment as illustrated in FIG. 7, the analyzing screen includes an area 202A in which the waveform that indicates the changes over time in three recorded biomedical signals (such waveforms correspond to biomedical data) is displayed together with annotations, and an area 202B in which analyzed data is displayed. In the present embodiment, the waveform that indicates the changes over time in three recorded biomedical signals is displayed on the analyzing screen. However, no limitation is intended thereby. For example, there are some cases in which input signals of a stimulator that generates a stimulus to be given to a test subject are displayed. For this reason, the number of signals is not limited to three. The area 202A in which the recorded signal waveform and the annotation data are displayed is arranged on the left side of the screen as viewed by the technician, and the area 202B on which analyzed data is displayed is arranged on the right side of the screen as viewed by the technician. As described above, it is desired that the area 202A and the area 202B be displayed simultaneously in parallel because during the analysis the analyst can easily and efficiently check or finalize the analytical results in the area 202B by operating, for example, a mouse, while checking or selecting a signal waveform in the area 202A.

In the present embodiment, the waveform of the magneto-encephalography (MEG) signals in the waveform display areas 101 and 102 are displayed above the screen of the waveform of the electrical signals in the waveform display area 103 of the area 202A. In the area 202B on the right side of the area 202A, the magneto-encephalogram distribution maps 141 and 142 are displayed on the topside of the screen area close to the area 202A, and the brain-wave distribution map 130 is displayed under the magneto-encephalogram distribution map 142. Accordingly, the analyst can train his/her line of sight from the waveform of the electrical signals in the waveform display area 103, to the waveform of the magneto-encephalography (MEG) signals in the waveform display areas 101 and 102, and then to the magneto-encephalogram distribution maps 141 and 142 and the brain-wave distribution map 130 (in a clockwise direction in the present embodiment). Due to this configuration, the analyst (or the technician) can train his/her line of sight efficiently, and thus the efficiency of analysis can improve. In the above description, the line of sight is moved in a clockwise direction. However, no limitation is intended thereby.

Next to the channel axis 104, the downsized images 141a, 142a, and 130a of the magneto-encephalogram distribution maps 141 and 142 and the brain-wave distribution map 130 are displayed, respectively. The downsized images are obtained by downsizing the magneto-encephalogram distribution maps 141 and 142 and the brain-wave distribution map 130, and displaying the setting conditions of the magneto-encephalogram distribution maps 141 and 142 and the brain-wave distribution map 130. For example, the regions of the downsized images 141a and 142a corresponding to the regions of the magnetic sensors selected on the magneto-encephalogram distribution maps 141 and 142 are brightened or darkened.

The area 202A includes the time-indicating area 110 in which the time data of the measurement is displayed in the horizontal direction (i.e., the first direction) of the screen, a time-slot display area 120, and the waveform display areas 101 to 103 in which the recorded signal waveforms are displayed in parallel on a type-of-signal by type-of-signal basis in the vertical direction (i.e., the second direction) of the screen.

In time-indicating area 110, the time axis 112 that indicates the lapse of time during the recording, and annotations 110a-7 and 110a-8 that are added along the time axis 112 are displayed.

In the time-slot display area 120, the time axis 122 that indicates the entire lapse of time during the recording is displayed. Moreover, a pointer mark 120a that indicates the point in time and to which an annotation is given and a time zone 120b indicating a time zone in which the signal waveforms that are currently displayed in the waveform display areas 101 to 103 are recorded are displayed along the time axis 122. Due to such display, the analyst can ascertain immediately at what time slot of the measurement and recording the signal waveforms that are being analyzed are obtained.

For example, the analyst may drag a time zone 120h on the bar of the time axis 122 after opening the analyzing screen. By so doing, the signal waveform in a desired time zone can be displayed in the waveform display areas 101 to 103. Alternatively, as will be described later in detail, the analyst may select a desired annotation from the annotation list 180. Due to this configuration, the display controller 251 can display the above-selected annotation and the signal waveform around the selected annotation in the waveform display areas 101 to 103.

In the waveform display areas 101 to 103, annotations A7 and A8 that are added to the signal waveforms during the recording are displayed. Marks 103a-7 and 103a-8 are highlighted, and the corresponding attribute icons 106-7 and 106-8 are displayed near the marks 103a-7 and 103a-8. Moreover, vertical lines 117-7 and 117-8 that indicate the points in time of the marks 103a-7 and 103a-8 are displayed. As the lines 117 are displayed, for example, when an annotation is given in association with the selection of a certain portion of the waveform display area 103, the analyst can visually recognize the results of selection easily also in the other signal display areas, i.e., the waveform display areas 101 and 102. The lines 117-7 and 117-8 enable easy visual recognition of the annotation data. In this sense, the lines 117-7 and 117-8 may be considered to be annotation data, and may be referred to as annotation lines.

In the analyzing screen illustrated in FIG. 7, the magneto-encephalogram distribution maps 141 and 142 that correspond to the signal waveforms displayed in the waveform display areas 101 and 102, respectively, and the brain-wave distribution map 130 that correspond to the signal waveform displayed in the waveform display area 103 are displayed. Moreover, an isomagnetic-field chart 150 (an example of a first distribution display area) of a magneto-encephalograph (MEG), an electrogram 160 of an electro-encephalograph (EEG), and a display window 190 for the tomographic images of the brain of a subject obtained in the magnetic resonance imaging (MRI) are displayed in the analyzing screen illustrated in FIG. 7. In the isomagnetic-field chart 150, a source area and a sink area of the magnetic field are displayed with coloring, and thus the direction in which the electric current flows can visually be identified. The isomagnetic-field chart 150 and the electrogram 160 are the data obtained after the measurement is completed, and the MRI tomographic images are separately obtained in an examination.

In the monitoring window 170, the live image of the subject during measurement is displayed in synchronization with the time at which the signal waveforms in the waveform display areas 101 to 103 are obtained. The analyst can analyze the signal waveforms while viewing the monitoring window 170 to check the state of the subject.

The annotation list 180 includes all the annotations added in the measurement recording. As the analyst clicks a desired one of annotation numbers 181 or a desired row, the display controller 251 can control the display to display the signal waveform in a desired time zone, including the point in time to which an annotation is given, in the waveform display areas 101 to 103 as illustrated in FIG. 7.

Unlike the measurement and recording screen, the analyst checks the signal waveform of annotated portion, and an estimation completion mark 182 is displayed for each of the annotations whose signal sources are finally estimated.

Figure 8:
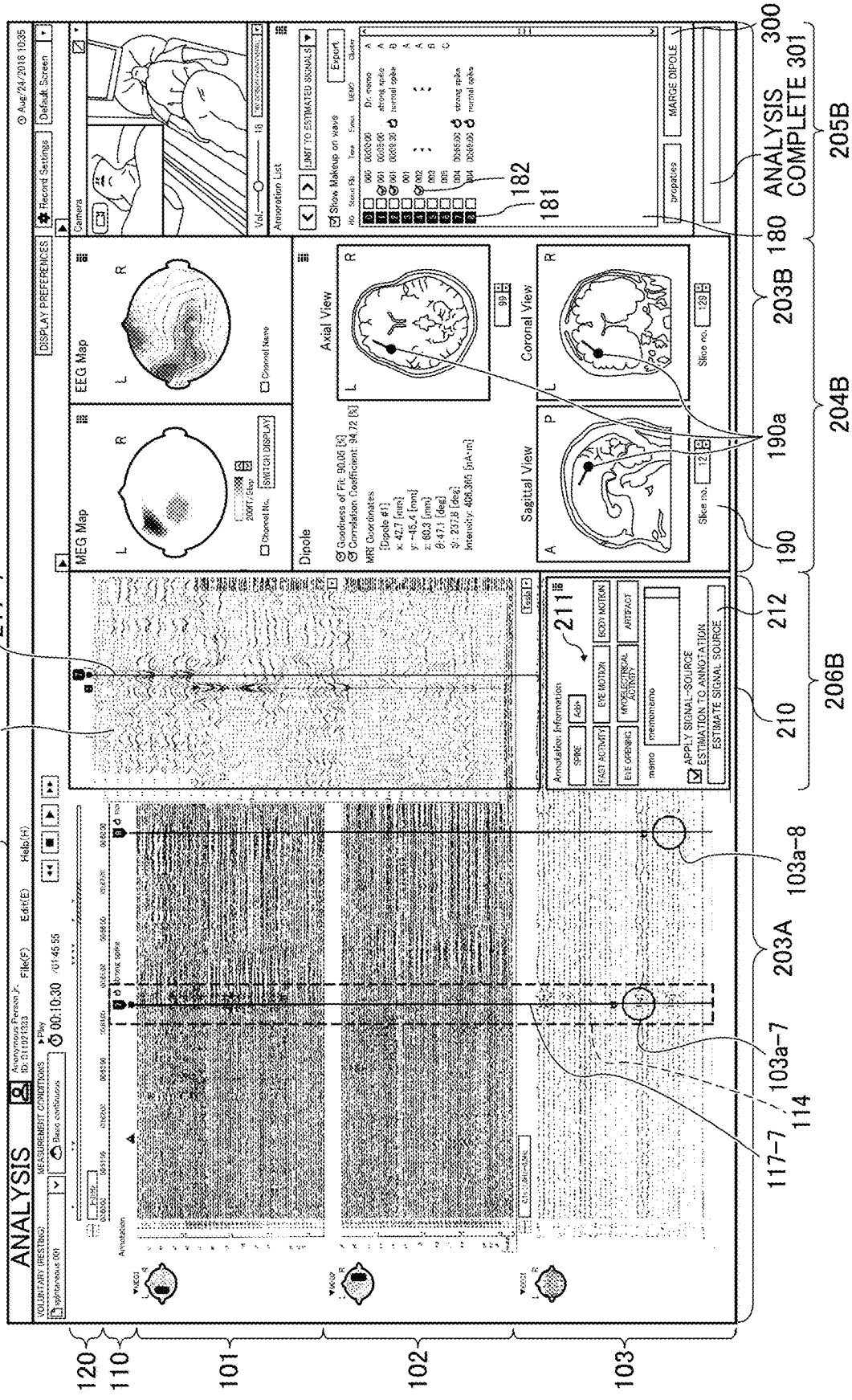
FIG. 8 is a diagram illustrating a screen displayed after a particular annotation line is selected on the screen of FIG. 7.

FIG. 8 is an overall view of the screen immediately after the line 117-7 is selected (for example, double-clicked) on the analyzing screen as illustrated in FIG. 7. Once the analyst focuses on the annotations A7 as illustrated in FIG. 7 and selects (for example, double clicks) the line 117-1 to analyze the waveform in that region, the display controller 251 magnifies the signal waveform near the highlighted signal waveform on the magnified display area 200 as illustrated in FIG. 8. The signal waveforms are magnified with the line 217-7 that indicates the point in time, across a predetermined time range indicated by an area 114.

As operated by the analyst, the display controller 251 causes the magnified display area 200 to magnify the signal waveforms. Due to this configuration, the analyst can reconfirm the relevance of the waveforms that correspond to the mark registered during the recording, or can check the waveforms that were not checked during the measurement and recording. For example, the line 217-7 may be dragged to the right or left side in order to specify or change the accurate point of waveform in question.

The type of signal waveform and the range of channel to be displayed on the magnified display area 200 can be designated. For example, the analyst moves his or her line of sight from the mark 103a-7 highlighted on the waveform display area 103 to the upper side of the screen, and checks whether there is a singular point in amplitude in the waveforms of the waveform display area 101 or 102 where the magnetoencephalographic waveforms are displayed. In such a configuration, the magnetoencephalographic waveform related to the mark 103a-7 can be magnified on the magnified display area 200 by specifying a target channel region in the waveform display area 101 or 102.

A check window 210 is displayed under the view of the magnified display area 200. The check window 210 includes attribute keys 211 for signal waveform and a signal-source estimation key 212. The attribute keys 211 correspond to the attribute information included in the pop-up window 115 on the measurement and recording screen, and the attribute keys 211 may be operated to select accurate attributes when the attribute registered when recording was performed is wrong. If the accurate position of the signal waveform and/or the selection of the attributes are confirmed, the estimation key 212 may be clicked to apply the estimation of signal source to the annotations. In other words, the information processing device 50 according to the present embodiment serves as an estimation unit and functions to estimate a signal source that corresponds to the annotation selected on the analyzing screen. The estimated signal source may be displayed over the tomographic image that corresponds to the estimated signal source from among the multiple tomographic images (live-subject tomographic images) of the brain of a subject obtained by magnetic resonance imaging (MRI).

When the position of the signal waveform and/or the attributes of a desired annotation are confirmed and the signal-source estimation key 212 is clicked in a configuration as illustrated in FIG. 8, an estimation completion mark 182 is added to the corresponding annotation in the annotation list 180. Further, a result of estimation 190a of a dipole is displayed on the MRI tomographic image in the display window 190.

Figure 9:
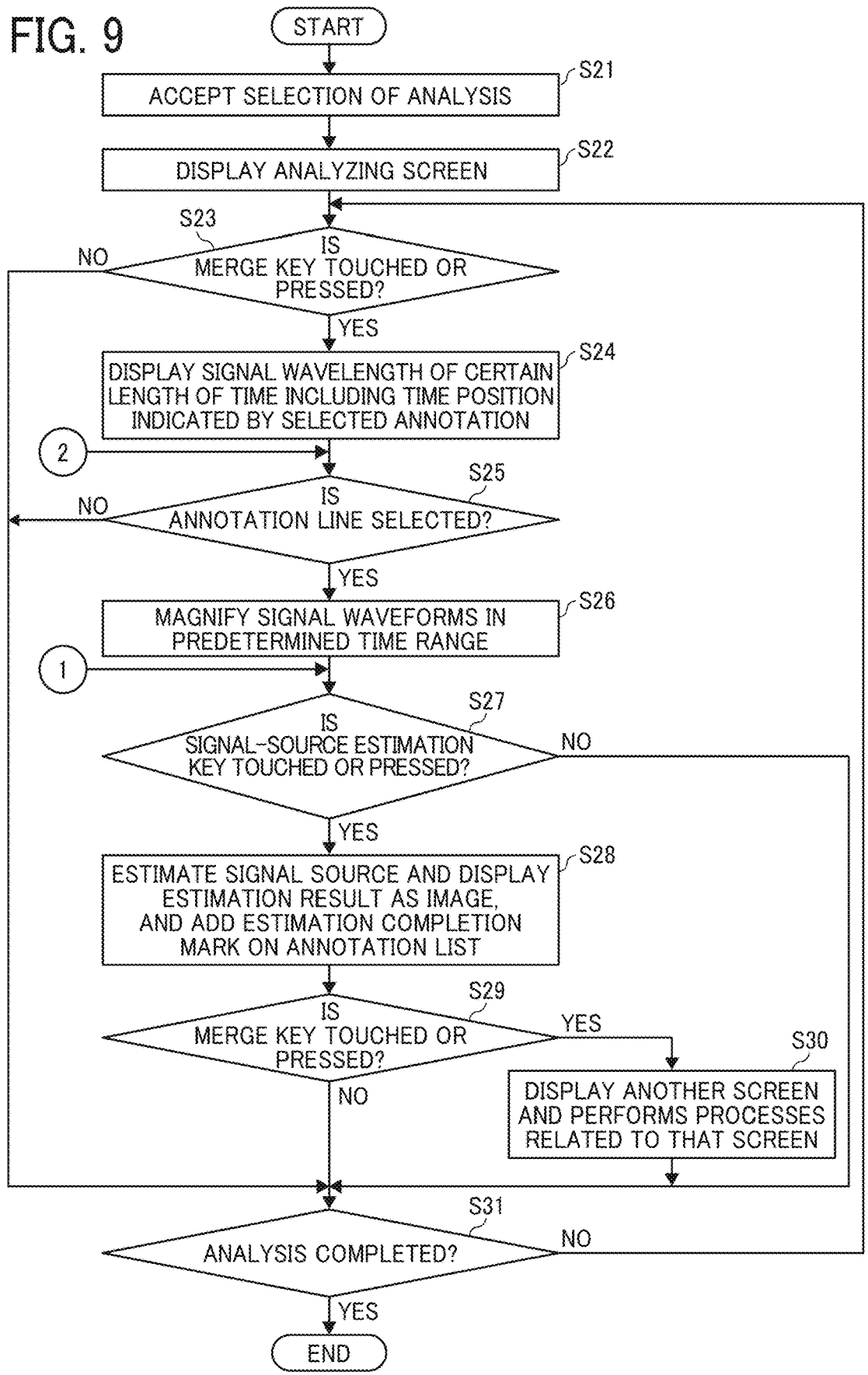
FIG. 9 is a flowchart of the operations performed by an information processing device during the analysis, according to an embodiment of the present disclosure.

FIG. 9 is a flowchart of display information processing performed by the information processing device 50 in a stage of analysis, according to the present embodiment. When "analysis" is selected on the starting screen 204 as illustrated in FIG. 2, the acceptance unit 52 of the information processing device 50 accepts the selection (step S21). Accordingly, the analysis is started, and the display controller 251 causes a display to display an analyzing screen (step S22). The initial analyzing screen may be a blank screen on which no signal waveform is displayed, or it may display signal waveforms in a predetermined time range at the beginning or end of the recording. Once an analyzing screen is displayed, the determining unit 259 determines whether a certain annotation is selected (step S23). The selection of an annotation may be the selection of a certain annotation number or a certain row in the annotation list 180, or may be the designation of a point in time by operating the time zone 120b along the time axis 122 of time-slot display area 120. When an annotation is selected (YES in step S23), the display controller 251 causes the display to display the signal wavelength of a certain length of time including the time position indicated by the selected annotation (S24).

The determining unit 259 determines whether the line 117 that indicates the time-position of the highlighted mark has been selected on the displayed screen (step S25). Once the line 117 has been selected ("YES" in step S25), as illustrated in FIG. 8, the display controller 251 magnifies the signal waveforms in a predetermined time range with the selected line (step S26). What is magnified is not necessarily limited to the signal waveform near the highlighted mark, and signal waveforms of different kinds at the same time-position may be magnified. For example, when a highlighted mark is given to waveforms of EEG signals, the magneto-encephalography (MEG) signal waveform at the same time-position may be magnified for view. Instead of magnifying the signal waveforms of all the channels, the signal waveforms obtained from a certain range of channel including the channel from which the marked signal waveform has been obtained may be magnified and displayed. In such a configuration, the presence or absence of specifying input operation on the type of signal waveform to be magnified and/or the range of channel may be determined.

Subsequently, the determining unit 259 determines whether a signal-source estimation key 212 as illustrated in FIG. 8 has been touched or pressed (step S27). When the signal-source estimation key 212 is touched or clicked ("YES" in step S27), the analyzer 252 estimates the signal source. The display controller 251 causes the display to display an estimation result 190a on the MRI tomographic image of the display window 190, and adds an estimation completion mark 182 on the annotation list 180 (step S28). Then, when touching or clicking of a merge dipole key 300 arranged under the annotation list 180 is accepted ("YES" in step S29), the display controller 251 causes the display to display another screen, and performs the processes related to that screen (step S30). When touching or clicking of a merge dipole key 300 is not accepted ("NO" in the step S29) or after the step S30, the determining unit 259 determines whether touching or clicking of the analysis complete key 301 has been accepted (step S31). When it is determined that no annotation has been selected ("NO" in the step S23), when no annotation line is selected for magnification ("NO" in the step S25), and when the signal-source estimation key is not touched or pressed ("NO" in the step S27), the process jumps to step S31 and whether or not to terminate the analysis is determined. The processes in the steps S23 to S30 are repeated until touching or clicking of the analysis complete key 301 is accepted ("YES" in step S31).

Whether or not the annotation has been changed may be determined between the steps S26 and S27. When it is determined that the annotation has been changed, the changes to the annotation list 180 are applied, and the process shifts to the determination process in the step S27.

As illustrated in FIG. 7 and FIG. 8, the waveform of the electrical signals in the waveform display area 103, the waveform of the magneto-encephalography (MEG) signals in the waveform display areas 101 102, and the magneto-encephalogram distribution maps 141 and 142 and the brain-wave distribution map 130 are collectively displayed in order of the clockwise direction. Due to this configuration, the relations between the multiple windows can efficiently be figured out with a small amount of motion of the line of sight.

However, on the analyzing screen, the magneto-encephalogram distribution maps 141 142 and the brain-wave distribution map 130 (these distribution maps will collectively be referred to as "display area 204B" in the following description) are displayed in the direction along which the time progresses (on the right side) of the waveforms of the magneto-encephalography (MEG) signals and the electro-encephalography (EEG) signals, and the monitoring window 170 and the annotation list 180 (these areas will collectively be referred to as "display area 205B" in the following description) are displayed on a further right side. For this reason, the widths of the waveform of the electro-encephalography (EEG) signals and the waveform of the magneto-encephalography (MEG) signals on the display are limited in the time-axial direction. Accordingly, the width of waveform that can be viewed at once may become truncated, degrading operability or analysis.

Figure 10:
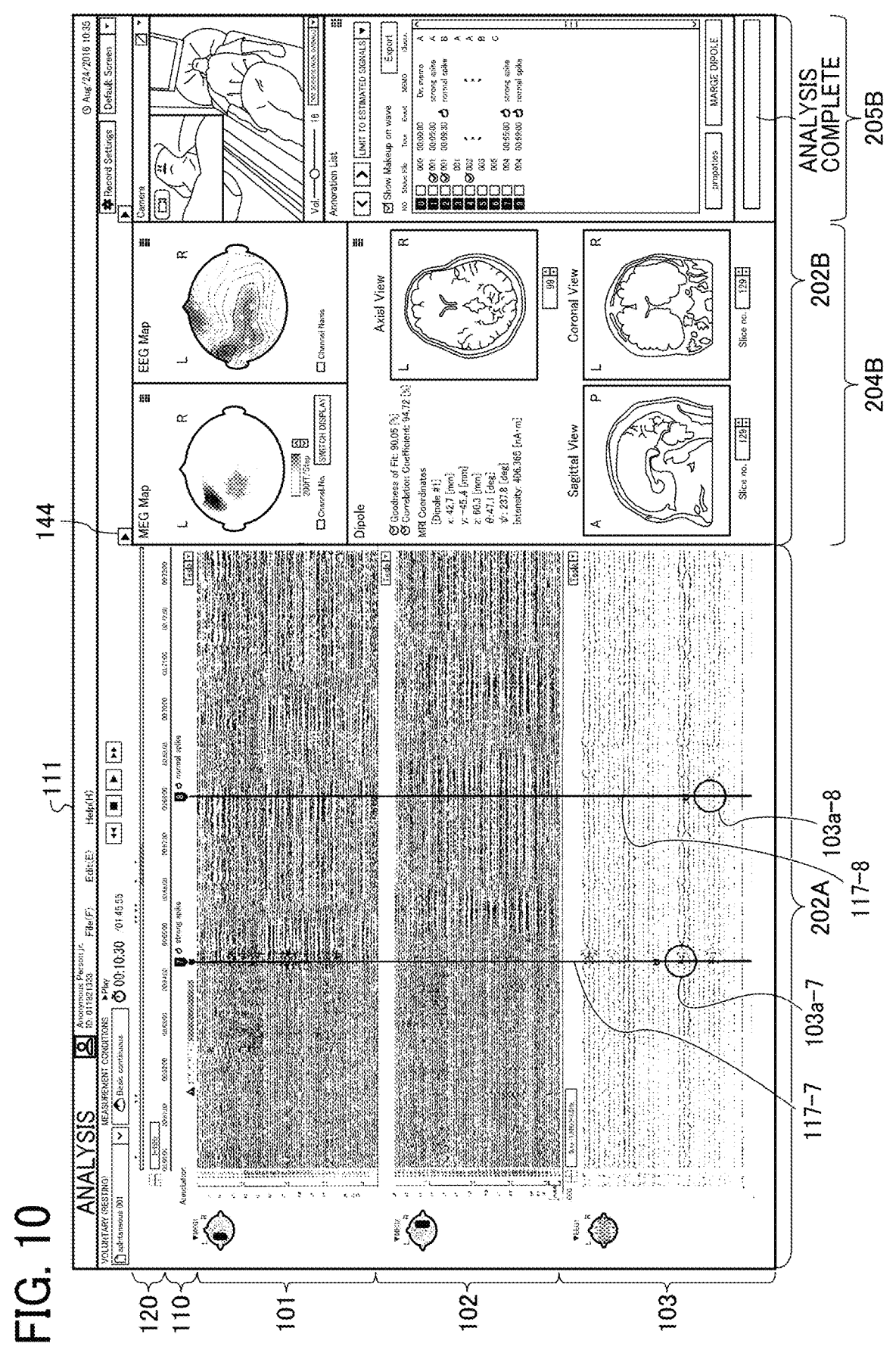
Figure 11:
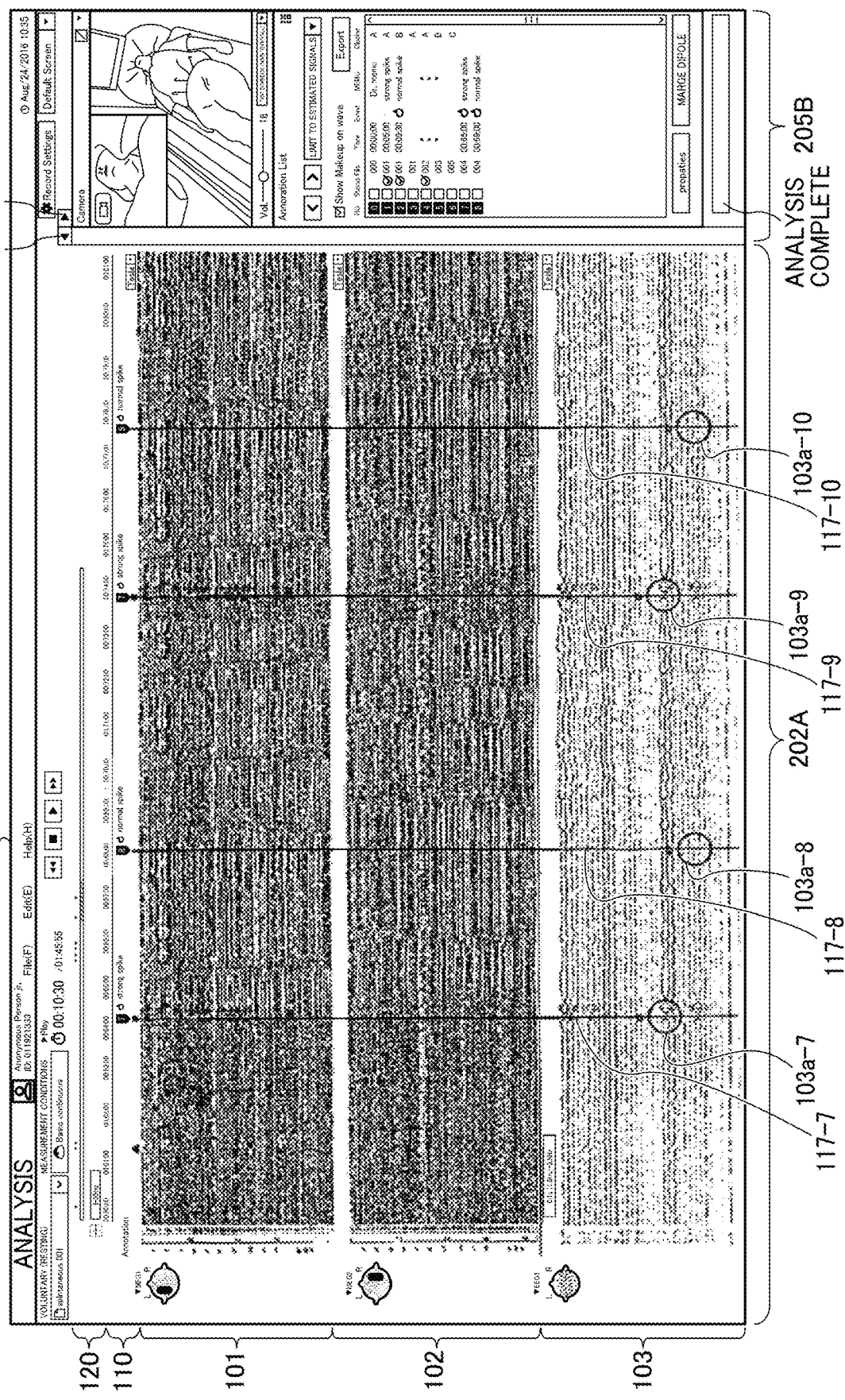
FIG. 11 is a diagram illustrating a screen displayed when display areas including an isomagnetic-field chart and an equipotential map are closed on the screen of FIG. 10.
Figure 12:
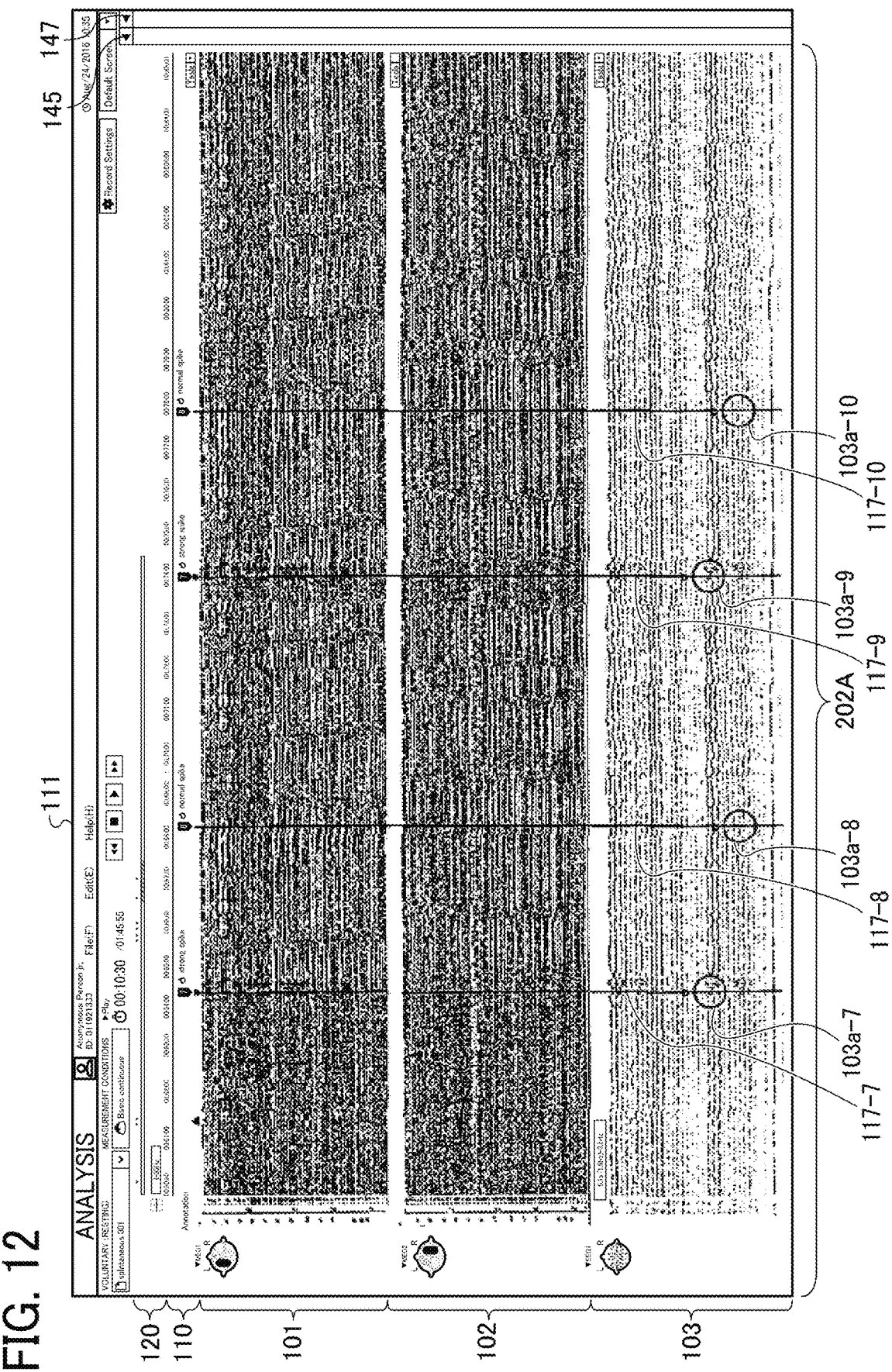
FIG. 12 is a diagram illustrating a screen displayed when display areas including a monitor are closed on the screen of FIG. 11.

In order to avoid such a situation, as illustrated in FIG. 10 to FIG. 12, the display area other than that of waveforms can be switched to be hidden from view such that the width of display of the waveform of the electro-encephalography (EEG) signals and the waveform of the magneto-encephalography (MEG) signals in the time-axial direction increases.

Firstly, once the analyst touches or clicks the window close key 143 on the analyzing screen as illustrated in FIG. 7, the display controller 251 causes the display to hide the magneto-encephalogram distribution maps 141 and 142 and the brain-wave distribution map 130 from view, as illustrated in FIG. 10. Then, the display controller 251 causes the display to extend the display of the waveforms displayed in the waveform display areas 101 to 103 to the area where the magneto-encephalogram distribution maps were displayed.

The waveforms as illustrated in FIG. 10 can be displayed wider than the waveforms FIG. 7 in the time-axial direction (in the width direction of the magneto-encephalogram distribution maps 141 and 142 and the brain-wave distribution map 130). Due to this configuration, longer waveforms can be viewed all at once. In this configuration, the downsized images 141a, 142a, and 130a of the magneto-encephalogram distribution maps 141 and 142 and the brain-wave distribution map 130 remain displayed. Accordingly, a state in which the settings can visually be recognized is maintained.

In this configuration, when any of the downsized images 141a, 142a, and 130a is touched or clicked on the analyzing screen as illustrated in FIG. 10, the display controller 251 causes the display to display the magneto-encephalogram distribution maps 141 and 142 and the brain-wave distribution map 130, as illustrated in FIG. 7. When the screen is switched from the state of FIG. 10 to the state of FIG. 7, it is desired that the start time of the waveforms displayed in the waveform display areas 101 to 103 in FIG. 7 be the same as the start time in FIG. 10. In such a configuration, the analyst recognizes as if the magneto-encephalogram distribution maps 141 and 142 and the brain-wave distribution map 130 are displayed over waveforms of later time displayed in the waveform display areas 101 to 103 in FIG. 7 (waveforms overlapping with an area where the magneto-encephalogram distribution maps 141 and 142 and the brain-wave distribution map 130 are arranged).

Accordingly, even when the magneto-encephalogram distribution maps 141 and 142 and the brain-wave distribution map 130 are switched between a displayed state and a hidden state, the positions at which the waveforms displayed in the waveform display areas 101 to 103 are displayed are unchanged. Accordingly, the workability or efficiency improves.

When the analyst touches or clicks the window close key 144 on the analyzing screen as illustrated in FIG. 10, the display controller 251 causes the display to hide the display area 204B (including the display window 190, the isomagnetic-field chart 150, and the equipotential map 160) from view as illustrated in FIG. 11. Then, the waveforms of the waveform display areas 101 to 103 are displayed also on the area where the display area 204B was displayed. When the screen is switched from FIG. 10 to FIG. 11, the window close key 144 is switched to a window open key 145.

The waveforms as illustrated in FIG. 11 can be displayed further wider than the waveforms of FIG. 10 in the time-axial direction (in the width direction of the display area 204B). Due to this configuration, longer waveforms can be viewed all at once.

Once the window open key 145 is touched or clicked on the analyzing screen as illustrated in FIG. 11, the display area 204B is displayed as illustrated in FIG. 10. When the screen is switched from the state of FIG. 11 to the state of FIG. 10, it is desired that the start time of the waveforms displayed in the waveform display areas 101 to 103 be the same between FIG. 11 and FIG. 10. In this configuration, the analyst recognizes as if the display window 190, the isomagnetic-field chart 150, and the equipotential map 160 are displayed over waveforms of later time displayed in the waveform display areas 101 to 103 (waveforms overlapping with an area where the display window 190, the isomagnetic-field chart 150, and the equipotential map 160 are arranged).

Accordingly, even when the display window 190, the isomagnetic-field chart 150, and the equipotential map 160 are switched between a displayed state and a hidden state, the positions at which the waveforms displayed in the waveform display areas 101 to 103 are displayed are unchanged. Accordingly, the workability or efficiency improves.

Subsequently, when the analyst touches or clicks the window close key 146 on the analyzing screen as illustrated in FIG. 11, the display controller 251 causes the display to hide the display area 205B (including the monitoring window 170 and the annotation list 180) from view as illustrated in FIG. 12. Then, the display controller 251 causes the display to display the waveforms of the waveform display areas 101 to 103 also in the area where the display area 205B was displayed. When the screen is switched from FIG. 11 to FIG. 12, the window close key 146 is switched to a window open key 147.

The waveforms as illustrated in FIG. 12 can be displayed further wider than the waveforms of FIG. 11 in the time-axial direction (in the width direction of the display area 205B). Due to this configuration, longer waveforms can be viewed all at once.

Once the window open key 147 is touched or clicked on the analyzing screen as illustrated in FIG. 12, the display controller 251 causes the display to display the display area 205B (including the monitoring window 170 and the annotation list 180) as illustrated in FIG. 11. When the screen is switched from the state of FIG. 12 to the state of FIG. 11, it is desired that the start time of the waveforms displayed in the waveform display areas 101 to 103 be the same between FIG. 12 and FIG. 11. In this configuration, the analyst recognizes as if the monitoring window 170 and the annotation list 180 are displayed over waveforms of later time displayed in the waveform display areas 101 to 103 (waveforms overlapping with an area where the monitoring window 170 and the annotation list 180 are arranged).

Due to this configuration, even when the monitoring window 170 and the annotation list 180 are switched between a displayed state and a hidden state, the positions at which the waveforms displayed in the waveform display areas 101 to 103 are displayed are unchanged. Accordingly, the workability or efficiency improves.

Figure 13:
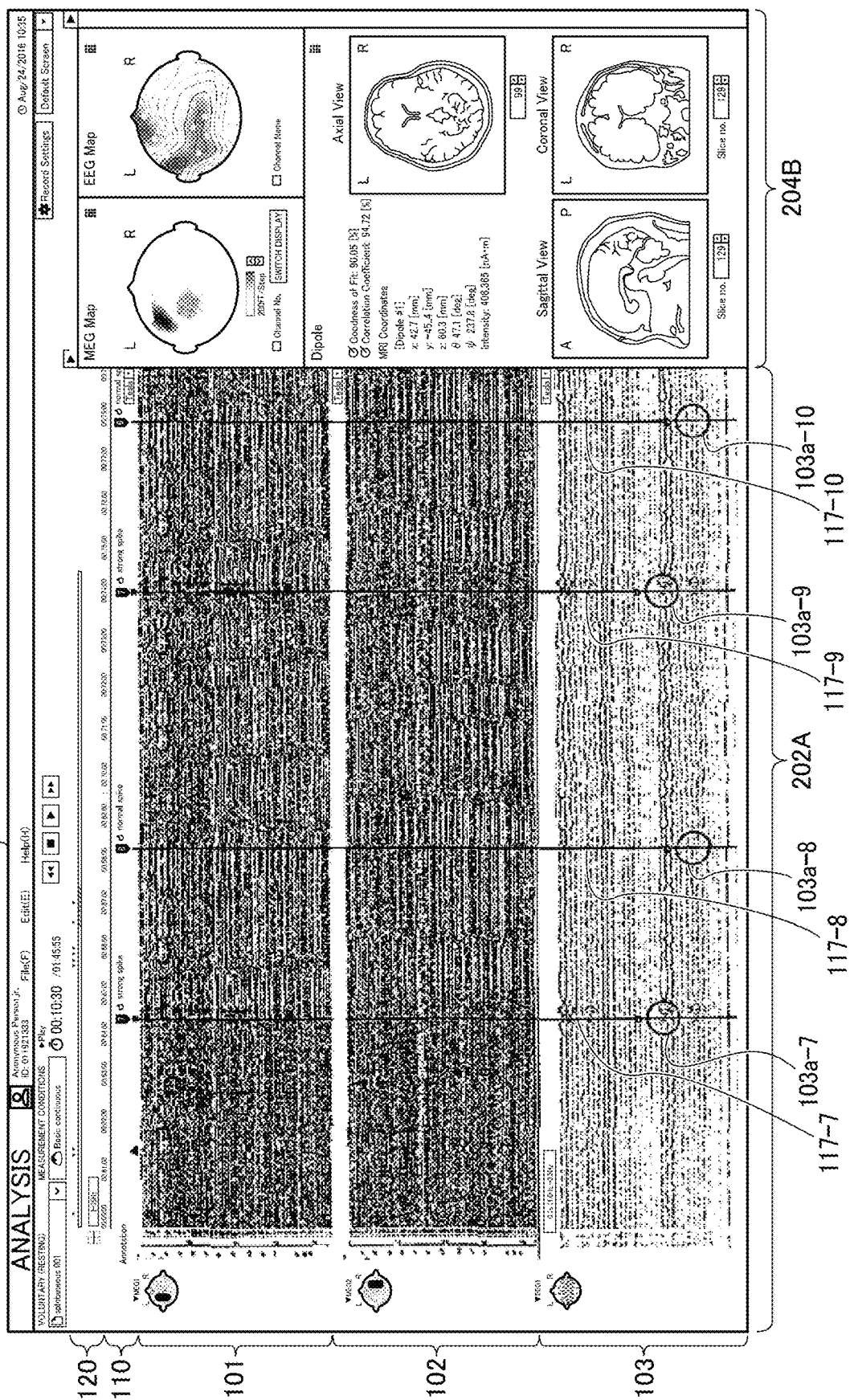
FIG. 13 is a diagram illustrating a screen displayed when display areas including an isomagnetic-field chart and an equipotential map are opened on the screen of FIG. 12.

As the analyst touches or clicks the window open key 145 on the analyzing screen as illustrated in FIG. 12, the display area 204B (including the display window 190, the isomagnetic-field chart 150, and the equipotential map 160) can be displayed while the display controller 251 keeps hiding the display area 205B (including the monitoring window 170 and the annotation list 180) from view as illustrated in FIG. 13.

As described above, the browsability of waveforms improves by increasing the width of waveform. However, for example, when the waveforms are analyzed by comparing the waveforms with the magneto-encephalogram distribution maps 141 and 142, the magneto-encephalogram distribution maps 141 and 142 need to be displayed every time the waveforms are to be displayed, and the operability or efficiency deteriorates.

First Embodiment

A first embodiment of the present disclosure is described below.

Figure 14:
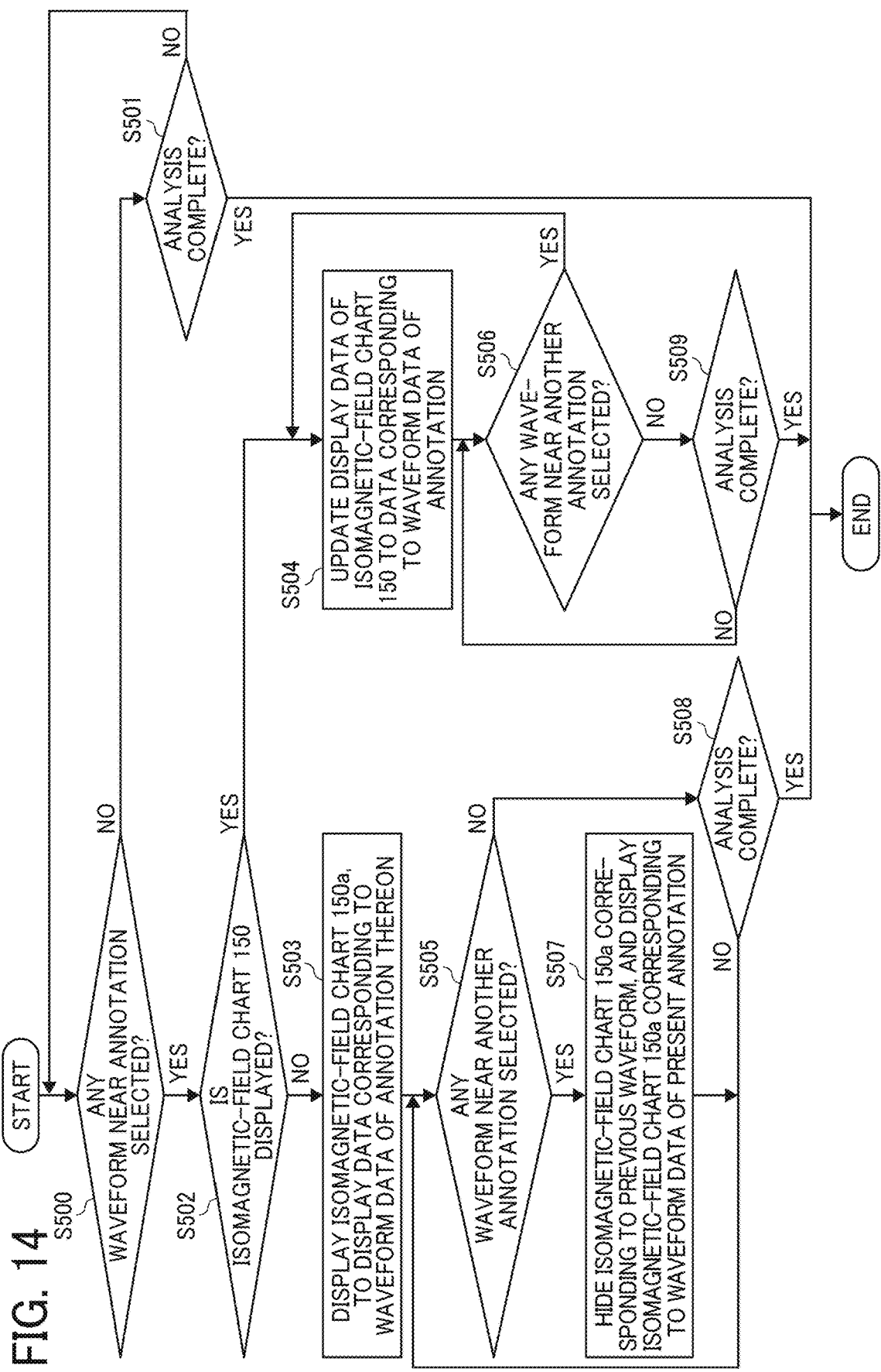
FIG. 14 is a flowchart of the operation performed by an information processing device, according to a first embodiment of the present disclosure.

FIG. 14 is a flowchart of the operations performed by the information processing device 50, according to the first embodiment. Note that all the displaying processes according to the following embodiments of the present disclosure (for example, displaying processes, hiding processes, and changing processes in display) are controlled by the display controller 251. Moreover, all the selecting processes are performed by an analyst, and all the determining processes are performed by the determining unit 259.

Once the analyst selects "analysis" on the starting screen 204 displayed on the information processing device 50 (as illustrated in FIG. 4), an analyzing screen is displayed. In the present embodiment, such an analyzing screen is one of those as illustrated in FIG. 7, FIG. 10, FIG. 11, and FIG. 12.

Whether the line 117 or the mark 103a that indicates the time-position of the highlighted mark has been selected is determined on the displayed analyzing screen (step S500). In the present embodiment, it is assumed that the selected line 117-7 or the selected mark 103a-7 is selected.

When selection of the lines 117 or the mark 103a is accepted ("YES" in the step S500), the determining unit 259 determines whether the isomagnetic-field chart 150 is displayed on the analyzing screen (step S502).

When the isomagnetic-field chart 150 is displayed on the analyzing screen as illustrated in FIG. 7, FIG. 10, and FIG. 13 ("YES" in the step S502), the display data of the isomagnetic-field chart 150, which is displayed on the analyzing screen, is updated to the display data of the isomagnetic-field chart 150 corresponding to the waveform data of the line 117-7 or the mark 103a-7 (step S504). Subsequently, when the line 117-8 or the mark 103a-8 that indicates the time-position of another highlighted mark is selected ("YES" in step S506), the display data of the isomagnetic-field chart 150 being displayed on the analyzing screen is updated to the display data of the isomagnetic-field chart 150 that corresponds to the waveform data of the line 117-8 or the mark 103a-8 (step S504). The processes in the steps S506 and S504 are repeated until touching or clicking of the analysis complete key 301 is accepted ("YES" in the step S509).

Next, when the isomagnetic-field chart 150 is not displayed on the analyzing screen as illustrated in FIG. 11 and FIG. 12 ("NO" in the step S502), an isomagnetic-field chart 150a-7 (i.e., an example of the second distribution display area), which is different from the isomagnetic-field chart 150 in the display area 204B, is displayed, and the data corresponding to the waveform data of the line 117-7 or the mark 103a-7 is displayed on the isomagnetic-field chart 150a-7 (step S503). Subsequently, when a line 117-10 or mark 103a-10 that indicates the time-position of another highlighted mark is selected ("YES" in step S505), the isomagnetic-field chart 150a-7 being displayed on the analyzing screen is hidden from view, and an isomagnetic-field chart 150a-10 that is different from the isomagnetic-field chart 150a-7 is displayed. Moreover, the display data of the isomagnetic-field chart 150a-10 is updated to the display data of the isomagnetic-field chart corresponding to the waveform data of the line 117-10 or the mark 103a-10 (step S507). Then, the processes in the steps S505 and S507 are repeated until touching or clicking of the analysis complete key 301 is accepted ("YES" in step S508).

When the lines 117 or the mark 103a that indicates the time-position of the highlighted mark is not selected ("NO" in the step S500), the processes in the step S500 are repeated until touching or clicking of the analysis complete key 301 is accepted ("YES" in step S501).

First Visual Display Example in Step S503

Figure 15:
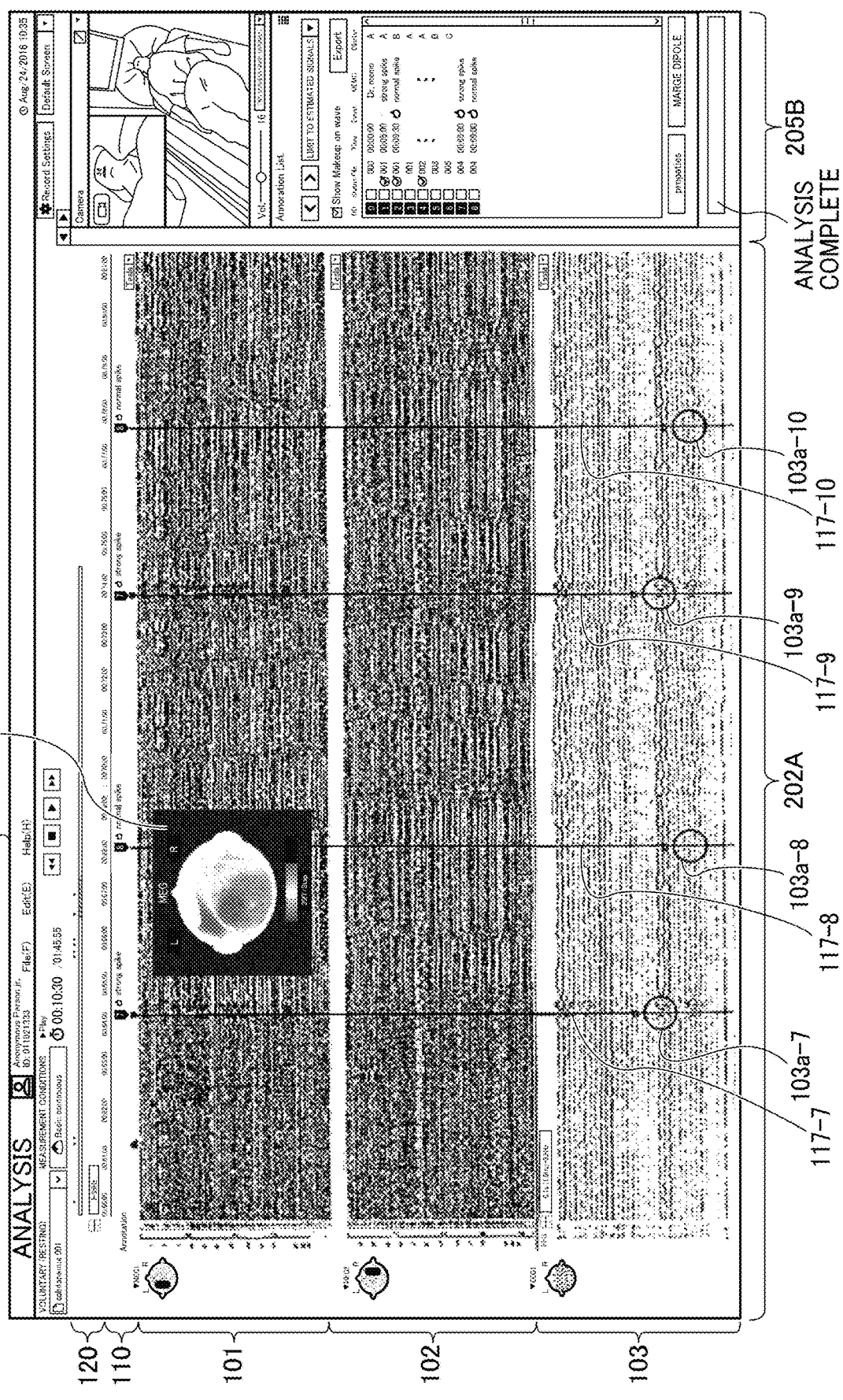
FIG. 15 is a diagram illustrating an analyzing screen according to the first embodiment of the present disclosure.

FIG. 15 is a diagram illustrating a visual display in the step S503 where the screen transition from FIG. 11 takes place, according to the present embodiment. An isomagnetic-field chart 150a-7 is displayed over the waveforms near the selected line 117-7 or the selected mark 103a-7 (more specifically, in a time domain later than the selected point in the time-axial direction). The display size of the isomagnetic-field chart 150a-7 is the same as the size of the isomagnetic-field chart 150 as illustrated in FIG. 7, FIG. 10, and FIG. 13. The background of the isomagnetic-field chart 150a-7 is brightened or darkened, and the waveforms in the waveform display areas 101 to 103 are made recognizable. In a similar manner to the isomagnetic-field chart 150, the external shape of the head is displayed in the isomagnetic-field chart 150a-7, and a source area and a sink area of the magnetic field are displayed inside the external shape of the head with coloring. Accordingly, the direction in which the electric current flows can visually be identified. The isomagnetic-field chart 150a-7 indicates the magnetic-field distribution that corresponds to the magneto-encephalography (MEG) waveform on the selected line 117-7, and the location of the brain activity can visually be predicted.

For example, the waveforms that are displayed on the electro-encephalography (EEG) signals in the waveform display area 103 are distinguished by different colors between the right and left sides of the head. Alternatively, the waveforms of the electro-encephalography (EEG) signals may be expressed in the same color, and the right and left sides of the head may be estimated based on the electrode numbers of the two points indicated in the vertical axis of the waveform. Accordingly, which one of the right and left sides of the head is active can be estimated to a certain extent based on the color being displayed on the waveform display area 103. Based on the comparison between this estimation and the site of brain activity predicted from the isomagnetic-field chart 150a-7, the relevance may be confirmed or denied. For example, when there is a source and sink on the right side of the isomagnetic-field chart 150a-7 when it was observed from the waveforms of the electro-encephalography (EEG) signals displayed on the waveform display area 103 that the left side of the head is activated, the prediction is in question. On the other hand, when there is a source and sink on the left side of the isomagnetic-field chart 150a-7, it is predicted that the relevance would be high.

As the isomagnetic-field chart 150a-7 is displayed near the selected point in time, the motion of the line of sight of an analyst can be minimized in the comparison between the isomagnetic-field chart 150a-7 and the selected waveforms, and the workability or efficiency improves. Further, the isomagnetic-field chart 150a-7 is displayed near the selected point in time of the magneto-encephalography (MEG) waveforms to be compared with, and thus the motion of the line of sight of an analyst can be minimized, and the workability or efficiency improves.

As known in the art, the analyst used to view the waveforms as illustrated in FIG. 11, and when there is a point in waveform that the analyst wishes to check, he or she touches or clicks the window open key 145 to control the display to display the display area 204B. Then, the analyst selects a point in waveform to update the display data of the isomagnetic-field chart 150.

By contrast, according to the present embodiment, as long as the waveforms as illustrated in FIG. 11 are viewed and a to-be-checked point in waveform is selected, the isomagnetic-field chart 150a to be compared with is displayed. Due to this configuration, the operability or efficiency improves.

Second Visual Display Example in Step S503

Figure 16:
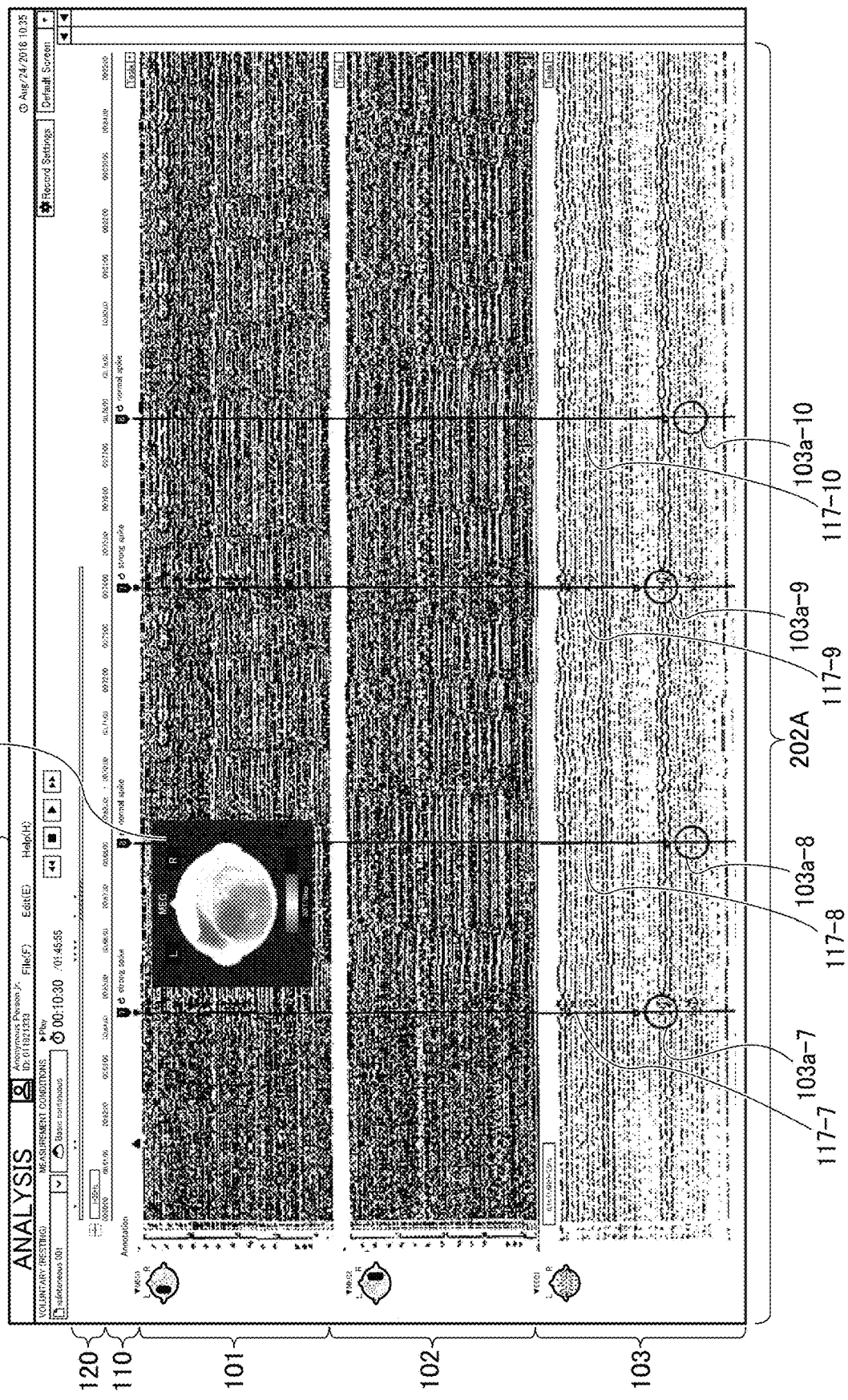
FIG. 16 is a diagram illustrating an analyzing screen according to the first embodiment of the present disclosure.

FIG. 16 is a diagram illustrating a visual display in the step S503 where the screen transition from FIG. 12 takes place, according to the present embodiment. In a similar manner to FIG. 15, the isomagnetic-field chart 150a-7 is displayed over the waveforms near the selected line 117-7 or the selected mark 103a-7 (more specifically, in a time domain later than the selected point in the time-axial direction).

In addition to the advantageous effects similar to those achieved in the configuration as illustrated in FIG. 15, the browsability of waveforms further improves compared with the configuration as illustrated in FIG. 15.

Visual Display Example in Step S507

Figure 17:
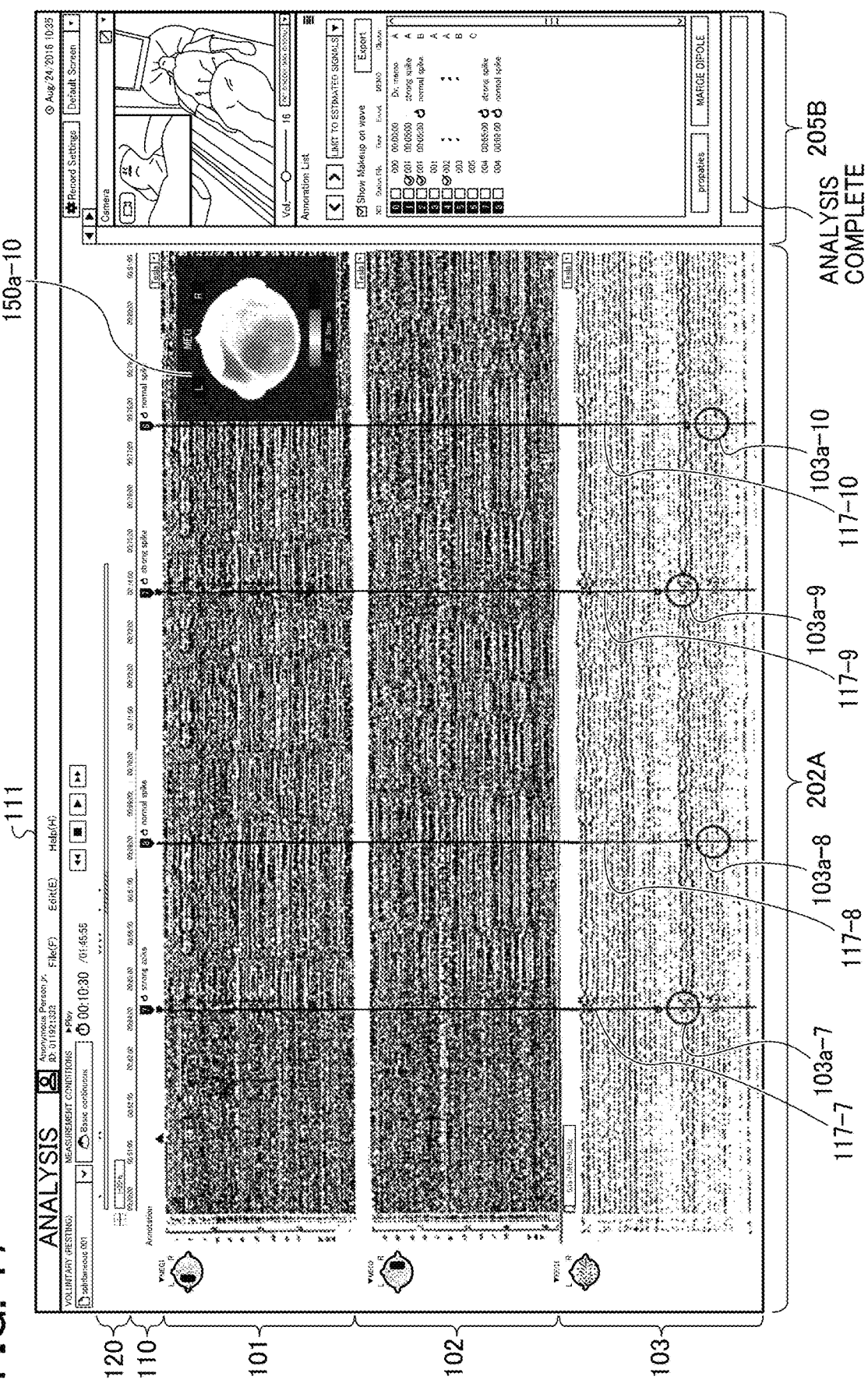
FIG. 17 is a diagram illustrating an analyzing screen according to the first embodiment of the present disclosure.

FIG. 17 is a diagram illustrating a visual display in the step S507 where the screen transition from FIG. 15 takes place, according to the present embodiment.

FIG. 17 illustrates a state in which the line 117-10 or the mark 103a-10 has been selected after the isomagnetic-field chart 150a-7 is displayed as illustrated in FIG. 15. In FIG. 17, the isomagnetic-field chart 150a-7 is closed, and the isomagnetic-field chart 150a-10 is displayed. Further, in FIG. 17, the display data of isometric-field chart 150a-10 has been updated to that of the isomagnetic-field chart corresponding to the waveform data of the line 117-10 or the mark 103a-10. Note that only the display of a source area and a sink area of the magnetic field is different between the isomagnetic-field chart 150a-10 and the isomagnetic-field chart 150a-7, and the size or external shape of the head and the background color are the same between the isomagnetic-field chart 150a-10 and the isomagnetic-field chart 150a-7. According to the present example case, advantageous effects similar to those in FIG. 15 can be achieved.

Note also that the configurations of display on the screen of FIG. 17 are applicable to the visual display example in FIG. 16.

No limitation is intended by the visual display example in FIG. 17, and for example, the isomagnetic-field chart 150a-10 may additionally be displayed while maintaining the display of the isomagnetic-field chart 150a-7.

Modification of First Embodiment

Figure 18:
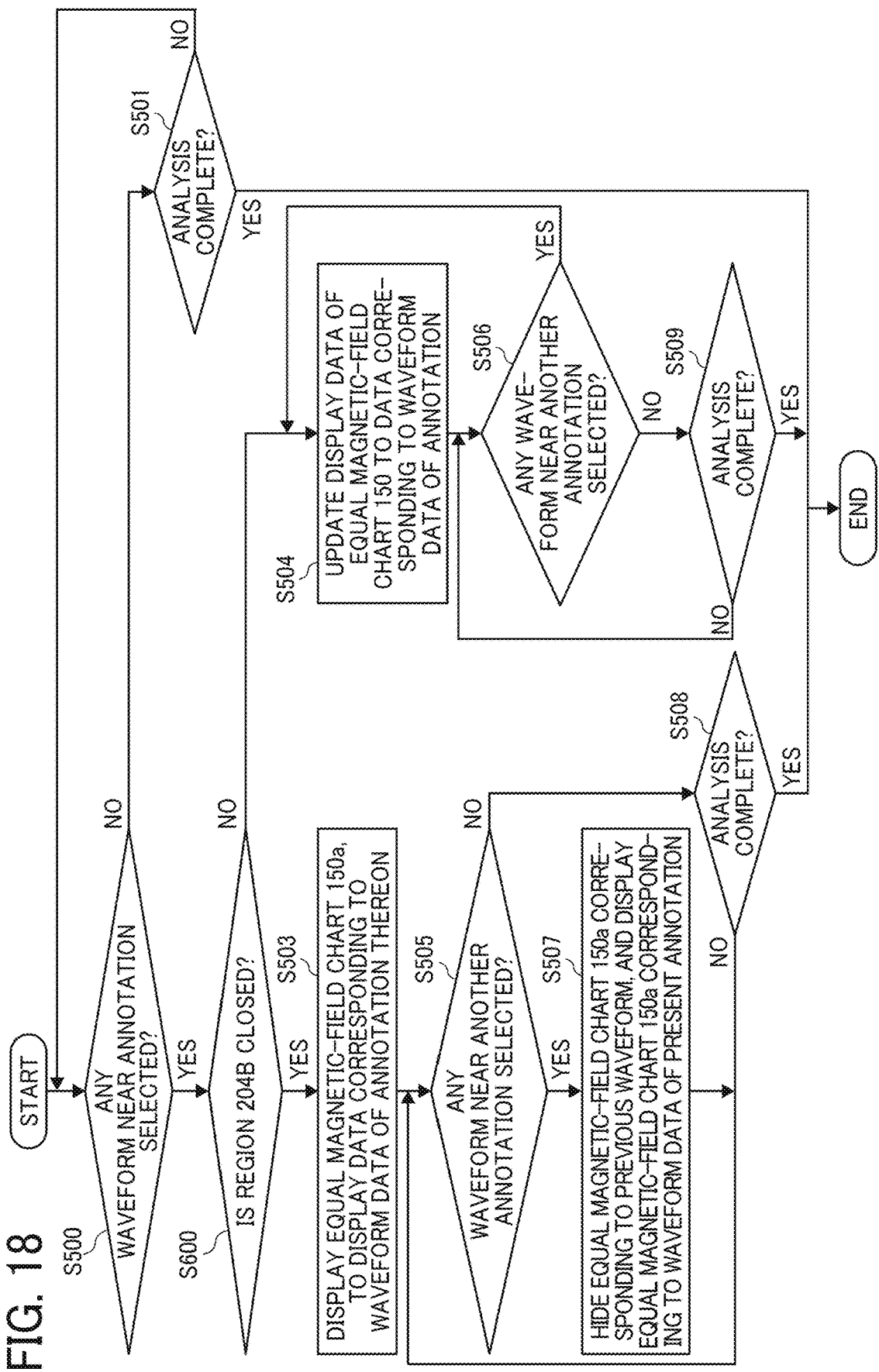
FIG. 18 is a flowchart of alternative operations performed by an information processing device, according to a modification of the first embodiment of the present disclosure.

FIG. 18 is a flowchart of alternative operations performed by the information processing device 50, according to a modification of the first embodiment of the present disclosure. In FIG. 18, like reference signs are given to steps similar to those illustrated in FIG. 14, and their detailed description is omitted.

In the first embodiment as described above, whether or not the isomagnetic-field chart 150 is being displayed is determined when selection of waveforms near an annotation is input.

In the present modification, whether or not the display area 204B is being displayed is determined (step S600). The display status of the display area 204B may be determined depending on whether the window open key 145 is maintained at a turned-on state or whether the window close key 144 is maintained at a turned-on state. Alternatively, the display status of the display area 204B may be determined based on the information about whether the window open key 145 or the window close key 144 is being displayed on the analyzing screen. Also in the present modification, advantageous effects similar to those of the flowchart of FIG. 14 can be achieved.

First Alternative Visual Display Example of Analyzing Screen According to First Embodiment In the step S503 according to the first embodiment, only the isomagnetic-field chart 150a is displayed (see FIG. 15 to FIG. 17). However, no limitation is intended thereby. For example, the equipotential map 160 of the electro-encephalograph (EEG) that corresponds to the waveform of the electro-encephalography (EEG) signals, from among the waveform of the electro-encephalography (EEG) signals and the waveform of the magneto-encephalography (MEG) signals, which constitute the selected waveforms as illustrated in FIG. 19 or FIG. 20, may be displayed together with the isomagnetic-field chart.

Figure 19:
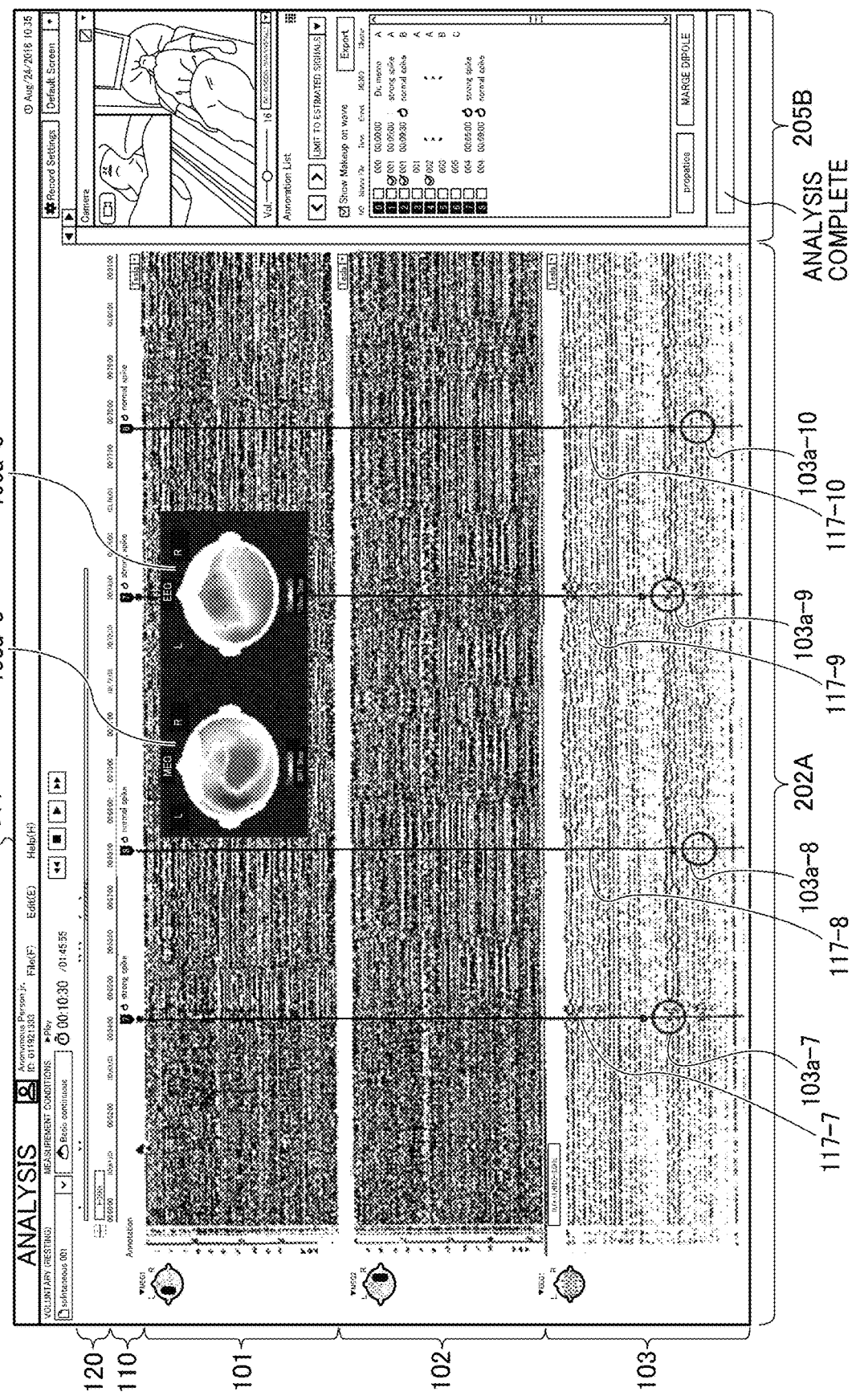
FIG. 19 is a diagram illustrating an alternative analyzing screen according to the first embodiment of the present disclosure.

FIG. 19 is different from FIG. 15 in that an equipotential map 160a of electro-encephalography (EEG) is added in FIG. 19. An isomagnetic-field chart and an equipotential map when the line 117-8 or the mark 103a-8 is selected are illustrated in FIG. 19.

Figure 20:
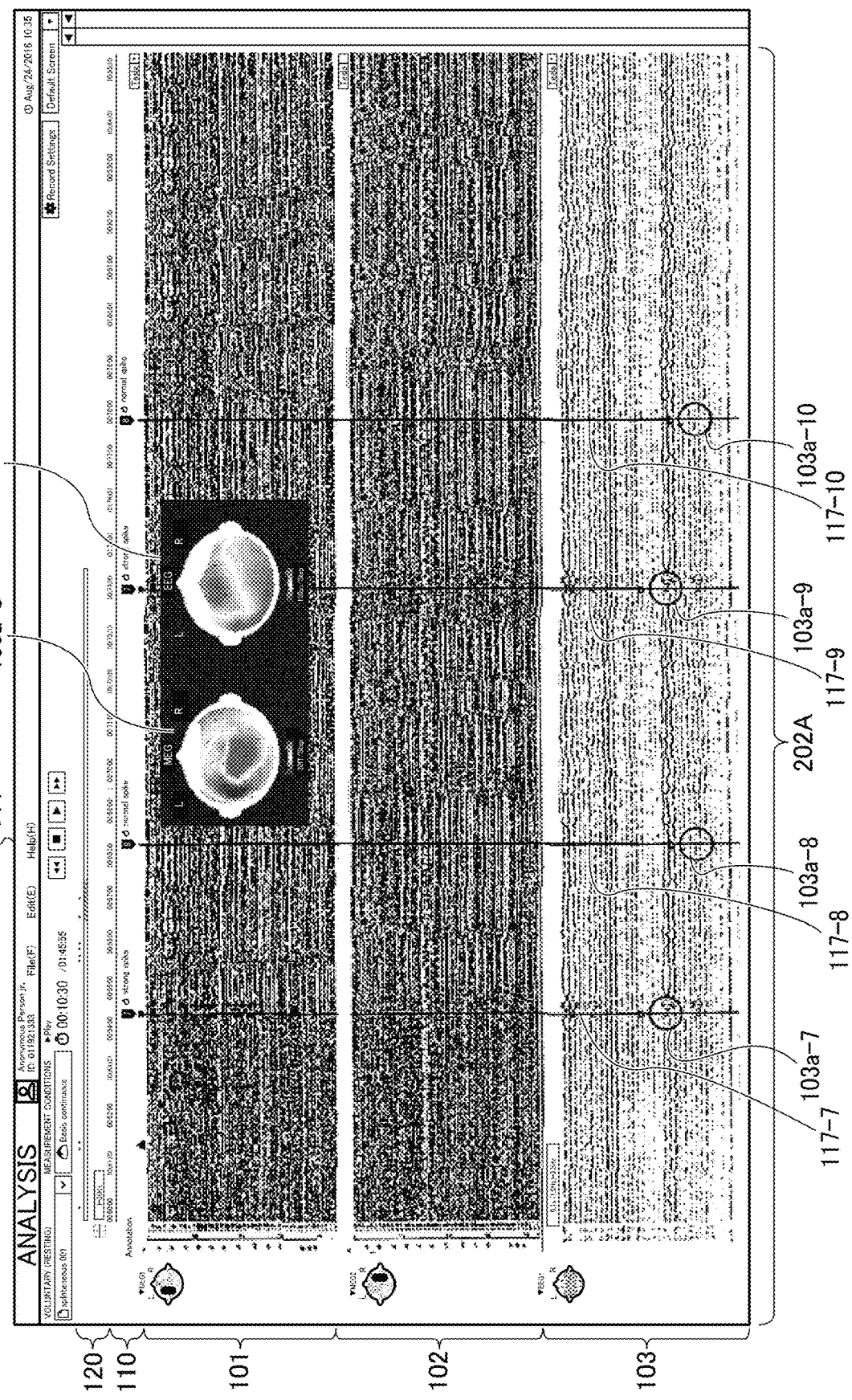
FIG. 20 is a diagram illustrating an alternative analyzing screen according to the first embodiment of the present disclosure.

FIG. 20 is different from FIG. 16 in that the equipotential map 160a of electro-encephalography (EEG) is added in FIG. 20. An isomagnetic-field chart and an equipotential map when the line 117-8 or the mark 103a-8 is selected are illustrated in FIG. 20.

According to the present example, in addition to the comparative verification as described above with reference to FIG. 15, the following things can be verified. First of all, when the line 117-8 or the mark 103a-8 is displayed at a point in waveform displayed in the display area where the amplitude is wide, it is difficult to determine whether such display is due to an epileptic seizure or a blink based on the shape of waveform. According to the present example, the relevance of whether the waveform is of epileptic seizures or of artifacts can be improved by checking an equipotential map 160-a8 that corresponds to the time of that waveform.

Moreover, the analyst can visually determine whether the direction of electric current that flows between two points of "+" and "−" in the distribution displayed on the equipotential map 160-a8 is orthogonal to the direction of electric current that flows between two points of a source and a sink in the distribution displayed on an isomagnetic-field chart 150a-8.

Figure 21:
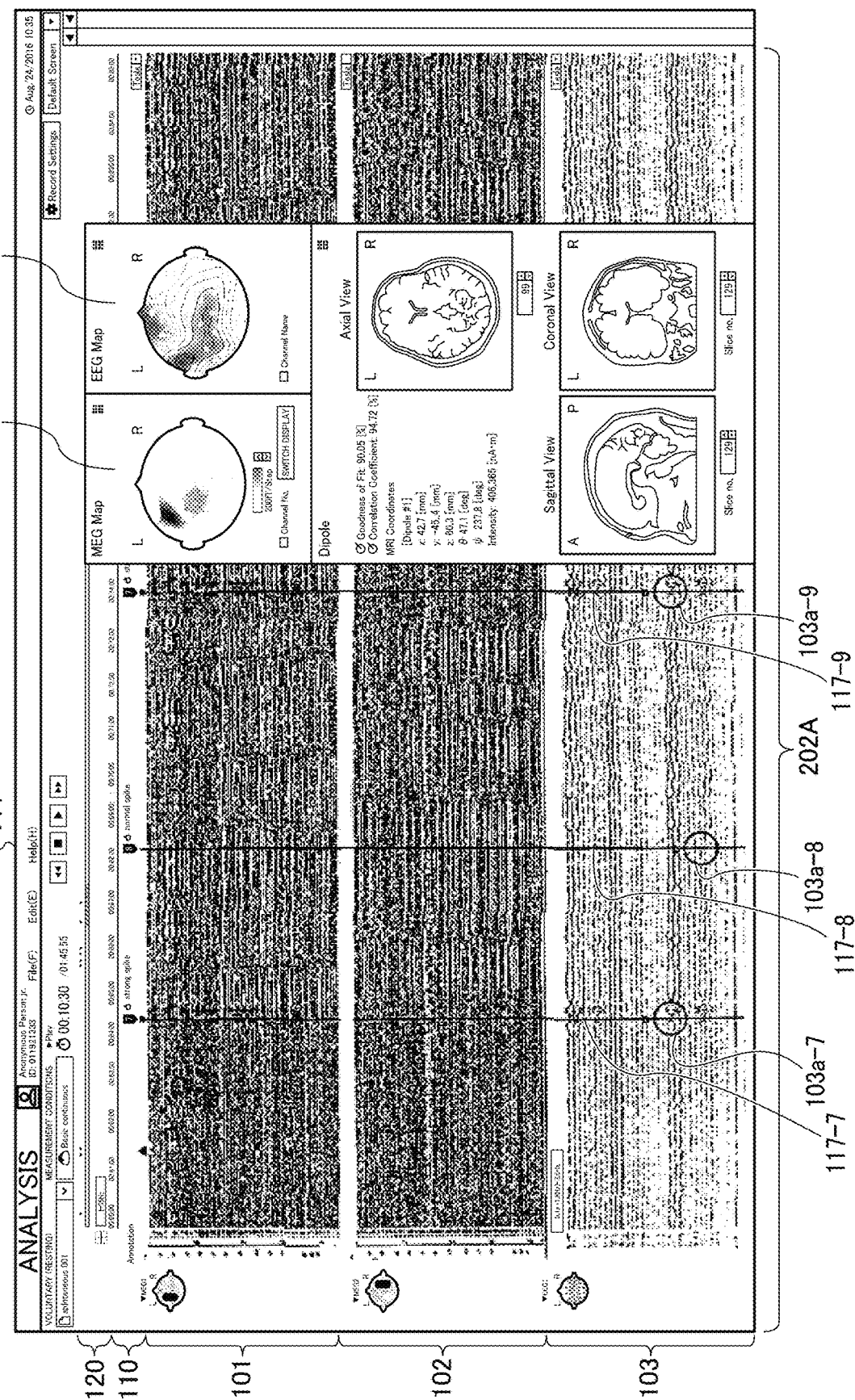
FIG. 21 is a diagram illustrating an alternative analyzing screen according to the first embodiment of the present disclosure.

Second Alternative Visual Display Example of Analyzing Screen According to First Embodiment In FIG. 21, the display window 190 for the tomographic images of the brain of a subject is displayed in addition to the items displayed in FIG. 19 and FIG. 20.

The items displayed in the present modification of the first embodiment are mostly the same as those of the display area 204B as illustrated in FIG. 7 and FIG. 8. However, the display area 204B is closed in FIG. 21, and a different window is displayed on the waveforms. In FIG. 21, the point in waveform selected from the lines 117 or the marks 103a, but the isomagnetic-field chart, the equipotential map, and the display window are displayed on the right side of the screen. Although the isomagnetic-field chart, the equipotential map, and the display window are displayed across the waveforms in the up-and-down directions, these items are displayed on the right side of the screen. Accordingly, the positions of the other annotations are visually recognizable.

According to the present example case, advantageous effects similar to those in FIG. 20 can be achieved.

Third Alternative Visual Display Example of Analyzing Screen According to First Embodiment Instead of the configuration as illustrated in FIG. 21, the items may be displayed as illustrated in FIG. 13. In such a configuration, when the lines 117 or the mark 103a are selected in the states as illustrated in FIG. 11 or FIG. 12, the window open key 145 is turned on, and items are displayed as illustrated in FIG. 13. The window open key 145 is manually turned on in the other examples. By contrast, in the present example, as the lines 117 or the mark 103a is selected, the display area 204B is automatically opened and displayed. Due to this configuration, the operability or efficiency improves, and advantageous effects similar to those in FIG. 21 can be achieved.

Figure 22:
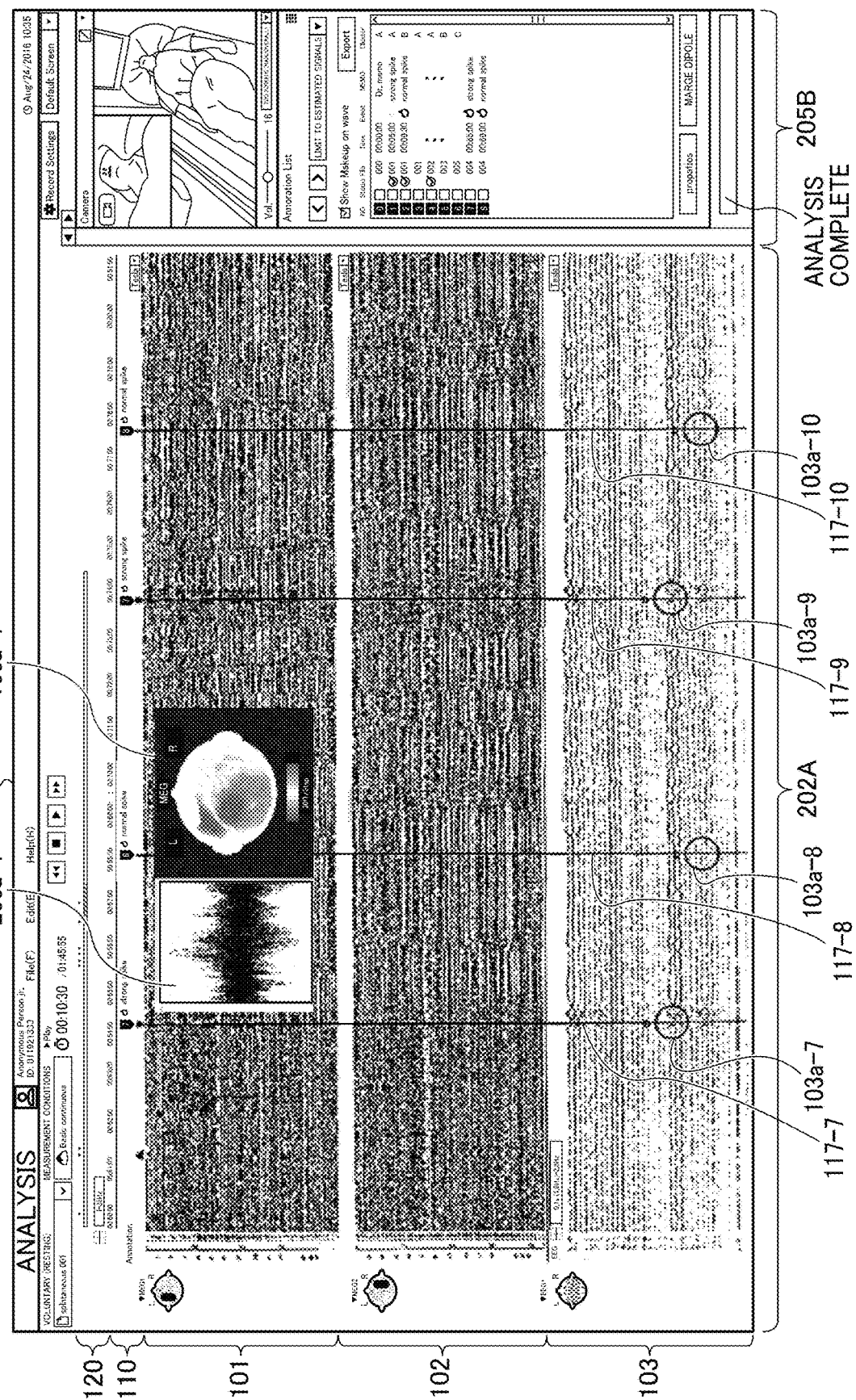
FIG. 22 is a diagram illustrating an alternative analyzing screen according to the first embodiment of the present disclosure.
Figure 23:
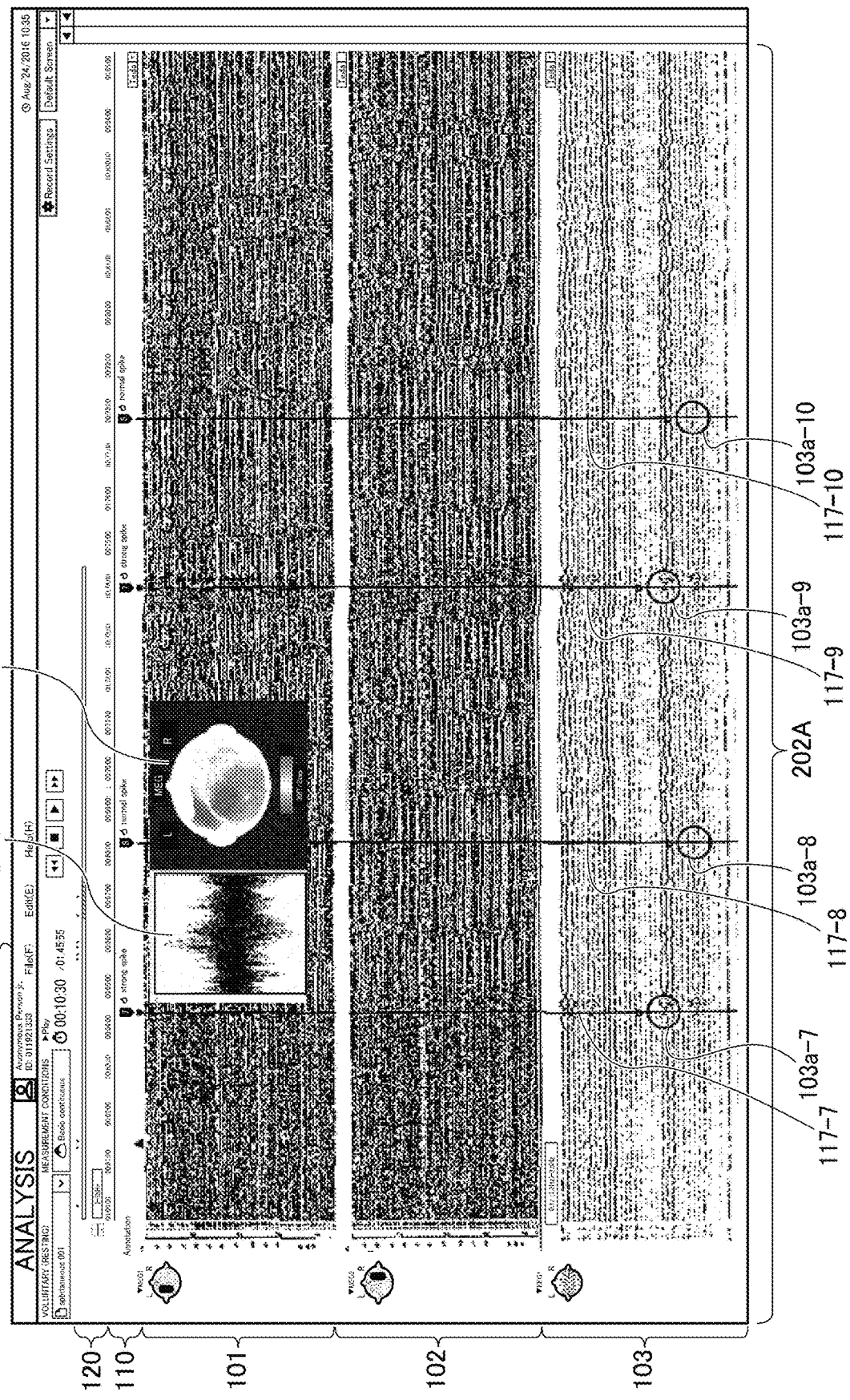
FIG. 23 is a diagram illustrating an alternative analyzing screen according to the first embodiment of the present disclosure.

Fourth Alternative Visual Display Example of Analyzing Screen According to First Embodiment Instead of the examples or embodiments as described above, the items may be displayed as illustrated in FIG. 22 or FIG. 23.

FIG. 22 and FIG. 23 are diagrams illustrating a state in which the window of a magnified display area 200a-7 and the isomagnetic-field chart 150a-7 that correspond to the selected one of the lines 117 or the marks 103a are displayed, according to a fourth alternative visual display example of the analyzing screen.

The display format of the magnified display area 200a-7 according to the present modification of the first embodiment is different from the display format of the magnified display area 200 as illustrated in FIG. 8. In the present example, the waveforms of to-be-displayed magneto-encephalography (MEG) signals (the waveforms displayed in the waveform display areas 101 and 102) are all superimposed on top of one another on a base of 0. Due to this configuration, the visibility of waveforms where the amplitude is relatively wide improves. Moreover, the width of the waveform of the magneto-encephalography (MEG) signals in the magnified display area 200a-7 in the vertical direction can be reduced. Accordingly, the window of the magnified display area 200a-7 and the isomagnetic-field chart 150a-7 can be placed side by side with the same height, and the viewability improves. According to the present example, advantageous effects similar to those in the isomagnetic-field chart 150a-8 as illustrated in FIG. 15 can be achieved, and the distribution of the isomagnetic-field chart can be compared with a magnified view of the corresponding magneto-encephalography (MEG) waveforms (displayed in the waveform display areas 101 and 102). Due to this configuration, whether the waveform is worth dipole estimation can be determined.

Fifth Alternative Visual Display Example of Analyzing Screen According to First Embodiment In FIG. 22 and FIG. 23, the window of the magnified display area 200a-7 and the isomagnetic-field chart 150a-7 are used merely for a view. Alternatively, a configuration as illustrated in FIG. 24 may be adopted.

Figure 24:
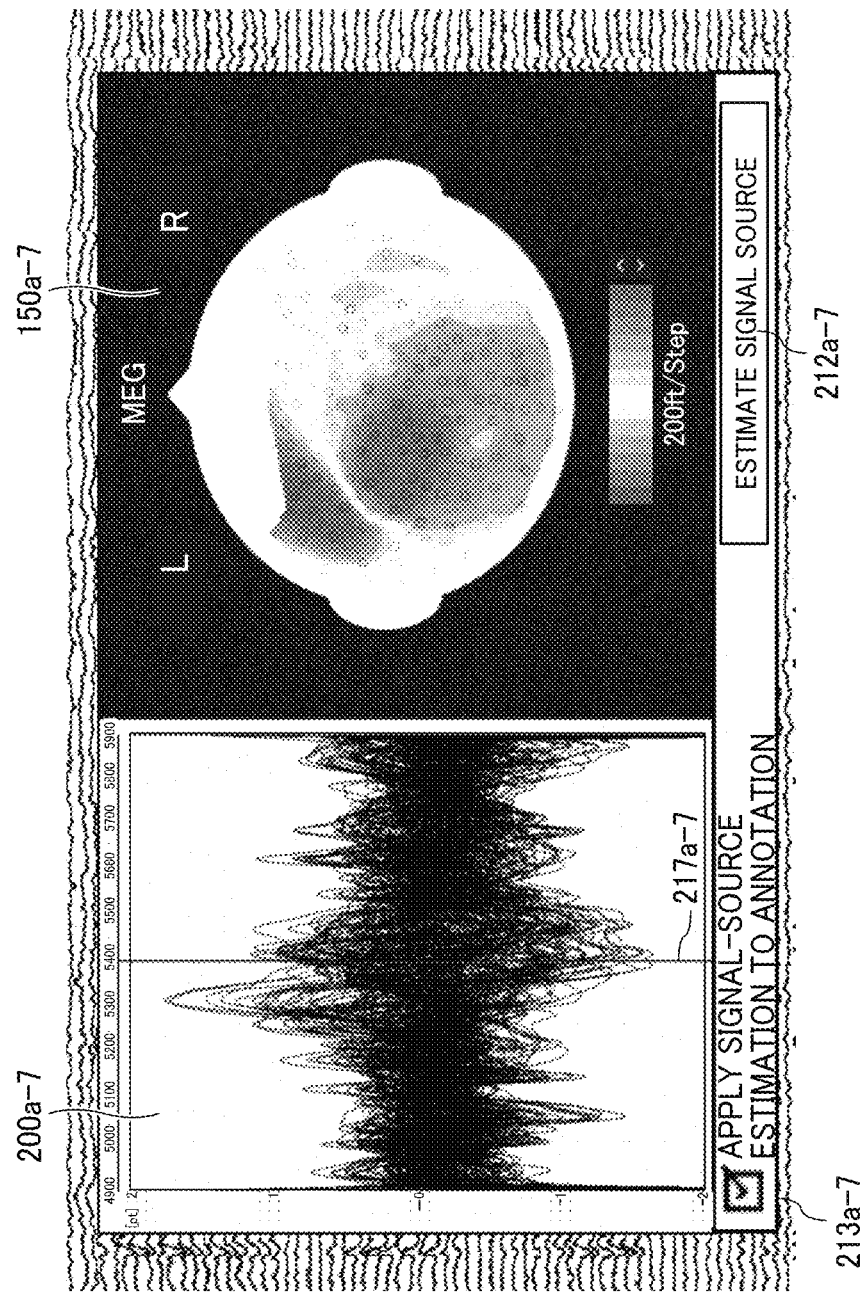
FIG. 24 is a diagram illustrating alternative display on the analyzing screen as illustrated in FIG. 23.

When the analyst focuses on the annotations as illustrated in FIG. 22 or FIG. 23 and the line 117-7 is selected to analyze the waveform in that region, the signal waveform near the highlighted signal waveform is magnified and displayed on the magnified display area 200a-7 as illustrated in FIG. 24. The signal waveforms are magnified and displayed with the line 217a-7 that indicates the point in time, across a predetermined time range including the line 117-7.

As a magnified view of the signal waveforms is displayed on the magnified display area 200a-7, the analyst can reconfirm the relevance of the waveforms that correspond to the mark registered during the recording. For example, the line 217a-7 may be dragged to the right or left side in order to specify or change the accurate point of waveform in question. In so doing, the display of a source area and a sink area of the magnetic field is also updated on the isomagnetic-field chart 150*a*-7 in synchronization with the operations of dragging the line 217*a*-7 to the right or left side.

A checkbox 213*a*-7 to determine whether or not to apply the estimation of signal source to the annotations and a signal-source estimation key 212*a*-7 are displayed under the view of the magnified display area 200*a*-7. Once the correct position of the signal waveform is confirmed, the analyst checks the checkbox 213*a*-7, and clicks the estimation key 212*a*-7. By so doing, the estimation of signal source can be applied to the annotations.

Once the accurate position of the signal source is specified on the magnified waveform as illustrated in FIG. 8 after the accurate position of the signal source has been confirmed on the window of the magnified display area 200*a*-7, the accurate position of the signal source needs to be adjusted again on the magnified waveform screen as illustrated in FIG. 8. By contrast, according to the present modification, the signal source can be estimated and the estimated signal source can be applied to the annotations on the accurate position of the signal waveform that is successfully confirmed on the magnified display area 200*a*-7. Accordingly, the operability or efficiency improves.

Second Embodiment

A second embodiment of the present disclosure is described below. Like reference signs are given to steps similar to those as described above, and their detailed description is omitted.

Figure 25:
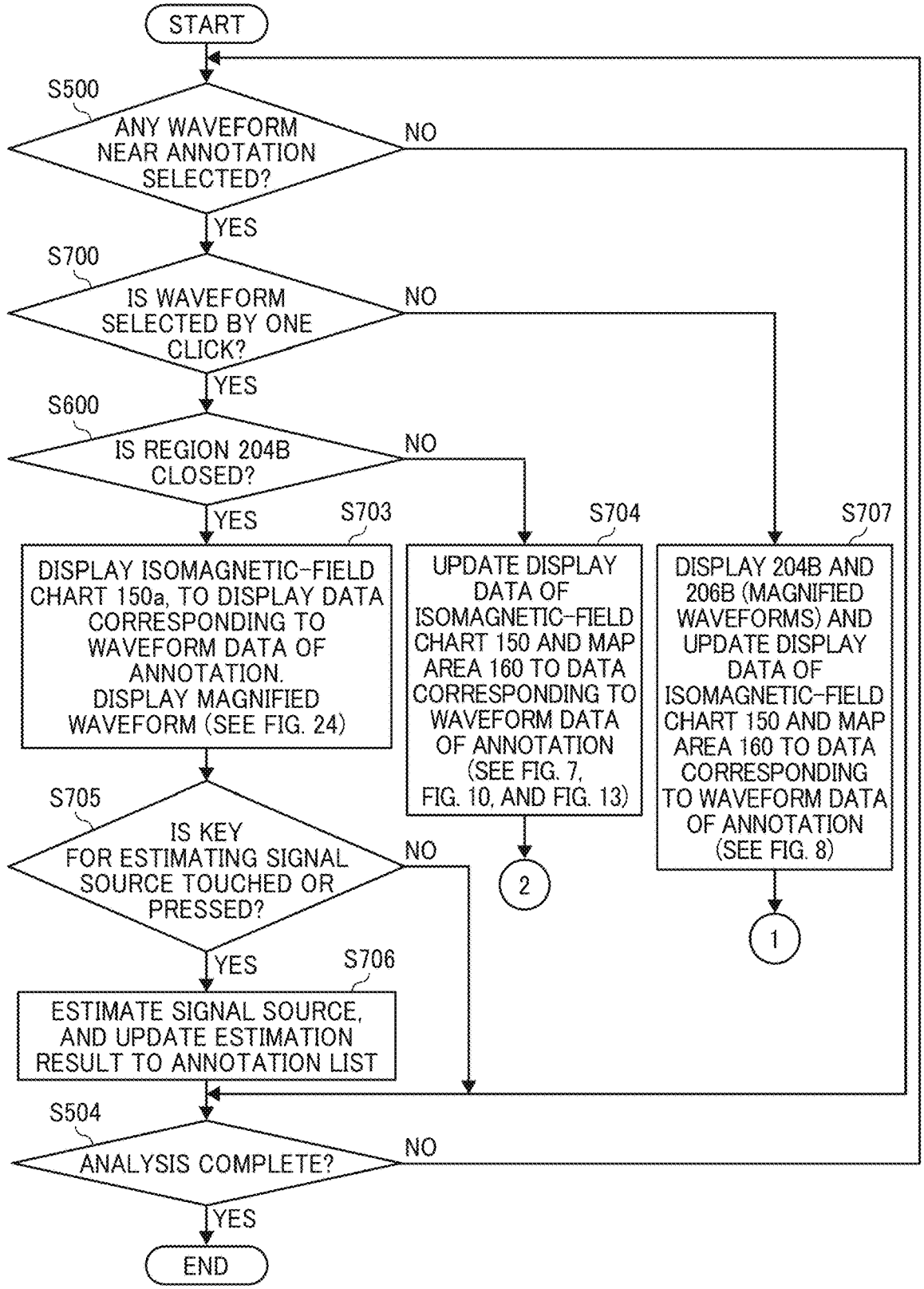
FIG. 25 is a flowchart of the operations performed by an information processing device, according to a second embodiment of the present disclosure.

FIG. 25 is a flowchart of the operations performed by the information processing device 50, according to the second embodiment of the present disclosure. An embodiment in which a different window opens depending on a difference in input data relating to selection of the line 117-7 or the mark 103*a*-7 is described with reference to FIG. 25.

When a waveform near the line 117-7 or the mark 103*a*-7 is selected ("YES" in step S500) and such selection is made by a double-click using a mouse ("NO" in step S700), the display area 204B and a display area (enlarged waveform) 206B are displayed, and the display data of the isomagnetic-field chart 150 and the equipotential map 160 are displayed upon being updated to the data corresponding to the waveform data near the line 117-7 or the mark 103*a*-7 (step S707). Then, the process shifts to step 27 as depicted in FIG. 9.

When a waveform near the line 117-7 or the mark 103*a*-7 is selected as in FIG. 25 ("YES" in step S500) and such selection is made by a single click using a mouse ("YES" in the step S700), whether or not the display area 204B is closed is determined (step S600).

When the display area 204B is closed ("YES" in the step S600), the window of the magnified display area 200*a*-7 and the isomagnetic-field chart 150*a*-7 are displayed as illustrated in FIG. 24 (step S703). Then, once a signal-source estimation key 212*a*-7 displayed under the screen of the enlarged display area 200*a*-7 is touched or clicked ("YES" in step S705), the signal source is estimated, and the result of estimation is applied to the annotation list (step S706).

When the display area 204B is open as illustrated in FIG. 7, FIG. 10, or FIG. 13 ("NO" in the step S600), the display data of the isomagnetic-field chart 150 and the equipotential map 160, which are being displayed, is updated to the data that corresponds to the waveform data obtained from the selected position (step S704). Then, the process shifts to step 25 as depicted in FIG. 9.

As described above, a different window is displayed depending on the data input when the waveforms near the line 117-7 or the mark 103*a*-7 is selected. Due to this configuration, the operability or efficiency of the visual display improves.

In the above description, a single-clicking and double-clicking are referred to as an example of input data. However, no limitation is intended thereby. For example, the input data may be a right-clicking and left-clicking with a mouse. Alternatively, the input data may be distinguished by the length of time (which may be short or long) while the mouse is being clicked. Further alternative methods may be adopted.

Modification of Second Embodiment

Figure 26:
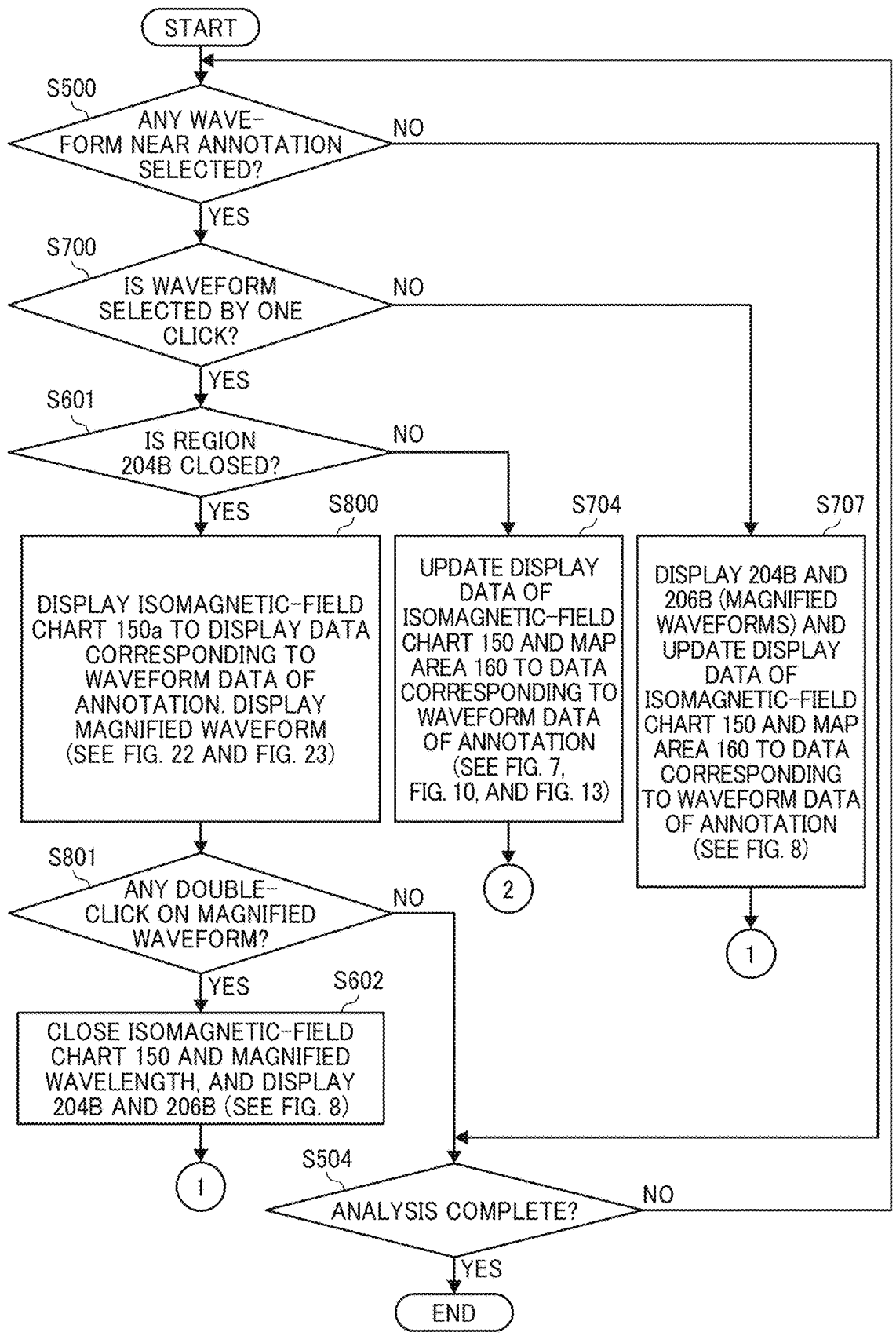
FIG. 26 is a flowchart of other operations performed by an information processing device, according to the second embodiment of the present disclosure.

FIG. 26 is a flowchart of alternative operations performed by the information processing device 50, according to a modification of the second embodiment of the present disclosure. The present modification of the second embodiment as illustrated in FIG. 26 is different from the embodiment as depicted in FIG. 25 in that the window of the magnified display area 200*a*-7 and the isomagnetic-field chart 150*a*-7 as illustrated in FIG. 22 and FIG. 23 are displayed (step S800) when the display area 204B is closed ("YES" in the step S601). Like reference signs are given to steps similar to those illustrated in FIG. 25, and their detailed description is omitted.

The line 217*a*-7 or the signal-source estimation key 212*a*-7, as illustrated in FIG. 24, are not displayed on the magnified display area 200*a*-7 according to the present modification.

Accordingly, when the analyst wishes to specify the accurate position of the signal waveform or estimate the signal source, the analyst uses a mouse to double-click a point on the screen of the magnified display area 200*a*-7 ("YES" in the S801). If such a double-click is done, the window of the magnified display area 200*a*-7 and the isomagnetic-field chart 150*a*-7 are closed, and magnified waveforms are displayed as illustrated in FIG. 8 (step S602). Then, the process shifts to the step 27 as depicted in FIG. 9 to estimate the signal source.

According to the present modification of the second embodiment, the signal source is estimated on a unified screen as illustrated in FIG. 8. Due to this configuration, the implementation of a program becomes easy, and the load of executing a program can be reduced. Note also that the double-click in the step S801 may be a single click.

Third Embodiment

A third embodiment of the present disclosure is described below.

In the previous embodiments or the modifications of those embodiments, the selected point in waveform is on or near the line 117-7 or the mark 103*a*-7. In the present embodiment, screen transition when the selected point in waveform is apart from the line 117-7 and the mark 103*a*-7 is described with reference to FIG. 27.

Figure 27:
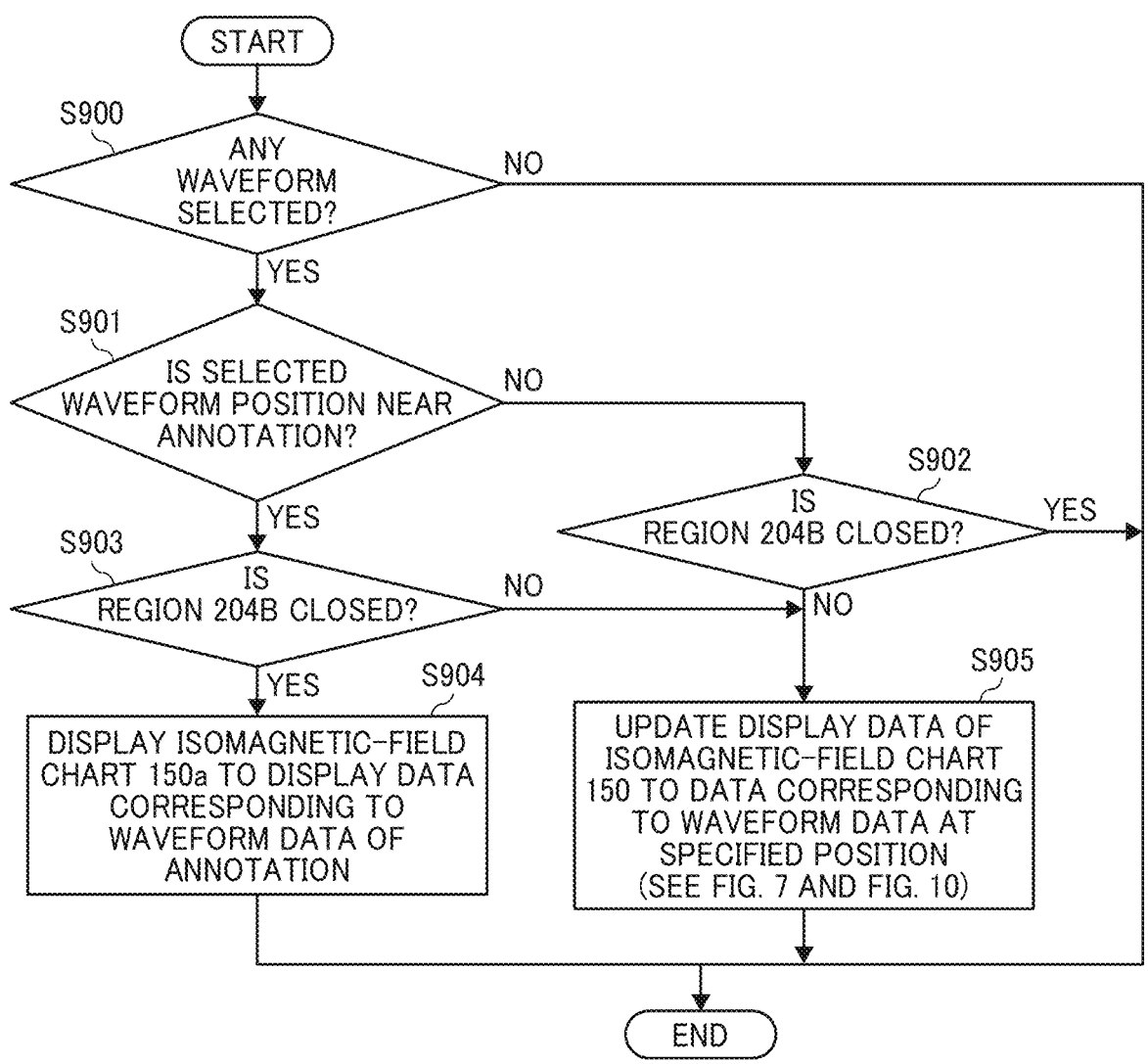
FIG. 27 is a flowchart of the operations performed by an information processing device, according to a third embodiment of the present disclosure.

FIG. 27 is a flowchart of the operations performed by the information processing device 50, according to the third embodiment of the present disclosure.

Once input data indicating the selection of a certain point of the waveforms displayed in the waveform display areas 101 to 103 of the analyzing screen is accepted ("YES" in step S900), whether the selected point in waveform is near the annotation (on the line 117-7 or the mark 103a-7 or near the line 117-7 or the mark 103a-7) is determined (step S901).

When the selected point in waveform is near the annotation ("YES" in the step S901) and the display area 204B is displayed on the analyzing screen ("NO" in step S903), the currently-displayed display data of the isomagnetic-field chart 150 is updated to the data that corresponds to the waveform data obtained from the specified point (step S905). On the other hand, when the display area 204B is not displayed on the analyzing screen ("YES" in the steps S903), the isomagnetic-field chart 150a is displayed, and then the data that correspond to the waveform data of the annotation is displayed.

When the selected point in waveform is not close to the annotation ("NO" in the step S901) and the display area 204B is displayed on the analyzing screen ("NO" in the step S902), the display data of the isomagnetic-field chart 150 is displayed upon being updated to the data corresponding to the waveform data of the specified point (step S905). On the other hand, when the display area 204B is not displayed on the analyzing screen ("YES" in the steps S902), the process is terminated without displaying the isomagnetic-field chart 150a.

Fourth Embodiment

A fourth embodiment of the present disclosure is described below. In the above-described embodiments or modifications of those embodiments, steps of determining whether the display area 204 or the isomagnetic-field chart 150 is being displayed or hidden from view on the analyzing screen after input data indicating the selection of a certain point of waveform is accepted are described. However, no limitation is intended thereby.

Figure 28:
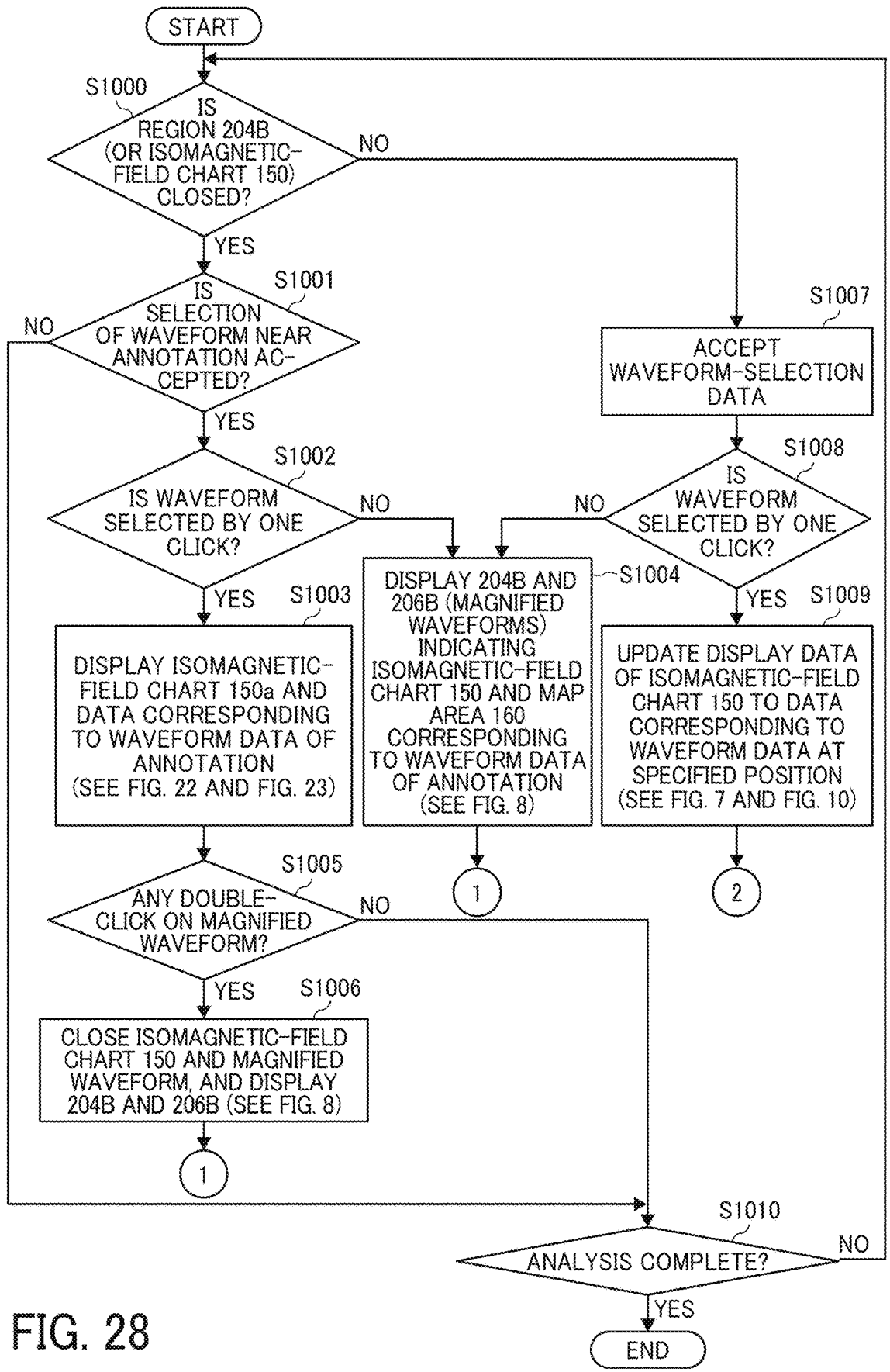
FIG. 28 is a flowchart of the operations performed by an information processing device, according to a fourth embodiment of the present disclosure.

FIG. 28 is a flowchart of the operations performed by the information processing device 50, according to the fourth embodiment of the present disclosure. For example, as illustrated in FIG. 28, a step of accepting input data indicating the selection of a certain point of waveform after whether the display area 204 or the isomagnetic-field chart 150 is displayed or hidden from view on the analyzing screen is determined (step S1000) may be adopted.

When the display area 204 or the isomagnetic-field chart 150 is being displayed ("NO" in the step S1000) and selection of waveform is accepted (step S1007) and the accepted selection is done by double-click using a mouse ("NO" in step S1008), as illustrated in FIG. 8, the display area 204B and the display area (enlarged waveform) 206B in which the isomagnetic field chart 150 and the map area 160 that correspond to the waveform data of the annotation are displayed are displayed (step S1004). On the other hand, when such selection accepted as above is made by a single click using a mouse ("YES" in the step S1008), the display data currently-displayed on the isomagnetic-field chart 150 as illustrated in FIG. 7 and FIG. 10 is updated to the data that corresponds to the waveform data obtained from the specified point (step S1009).

When the display area 204 or the isomagnetic-field chart 150 is hidden from view ("YES" in the step S1000) and the input data indicating the accepted selection of waveform does not indicate a point in waveform on an annotation or near the annotation ("NO" in step S1001), the display area 204 or the isomagnetic-field chart 150 remain hidden from view.

By contrast, when the input data indicating the accepted selection of waveform indicates a point in waveform on an annotation or near the annotation ("YES" in the step S1001) and the accepted selection is done by double-click using a mouse ("NO" in step S1002), as illustrated in FIG. 8, the display area 204B and the display area (enlarged waveform) 206B, which indicate the isomagnetic field map 150 and the map area 160 that correspond to the waveform data of the annotation are displayed, are displayed (step S1004).

When such selection as above is made by a single click using a mouse ("YES" in the step S1002), the isomagnetic-field chart 150a is displayed as illustrated in FIG. 22 or FIG. 23, and the data that correspond to the waveform data of the annotation is displayed (step S1003). After that, once the input data indicating that the magnified display area 200a has been double-clicked by a mouse is accepted, the magnified display area 200a and the isomagnetic-field chart 150a are closed, and as illustrated in FIG. 8, the display area 204B and the display area (enlarged waveform) 206B, which indicate the isomagnetic-field map 150 and the map area 160 that correspond to the waveform data of the annotation are displayed, are displayed (step S1006).

Figure 29:
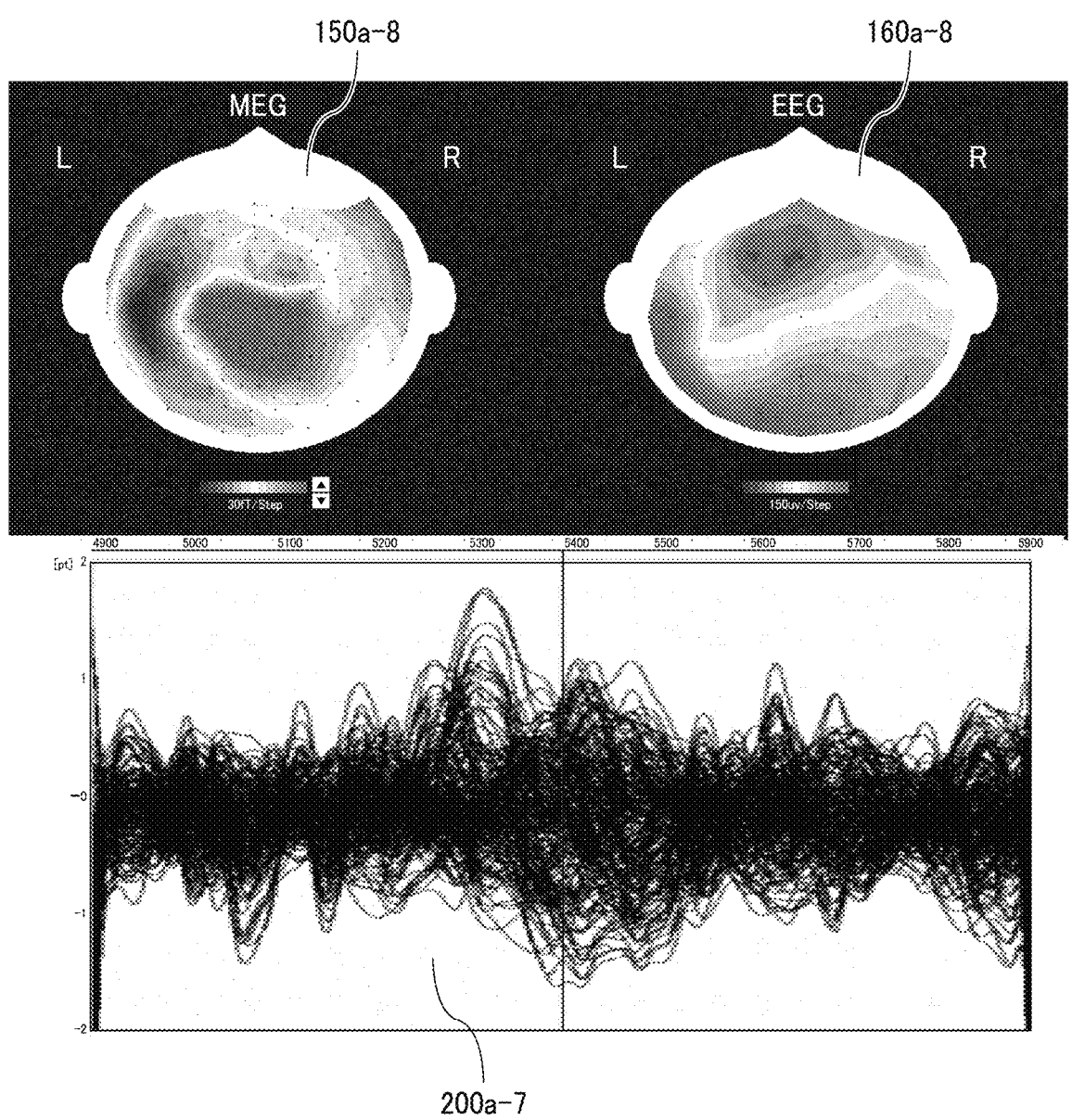
FIG. 29 is a diagram illustrating an alternative display displayed on an analyzing screen, according to an embodiment of the present disclosure.
Figure 30:
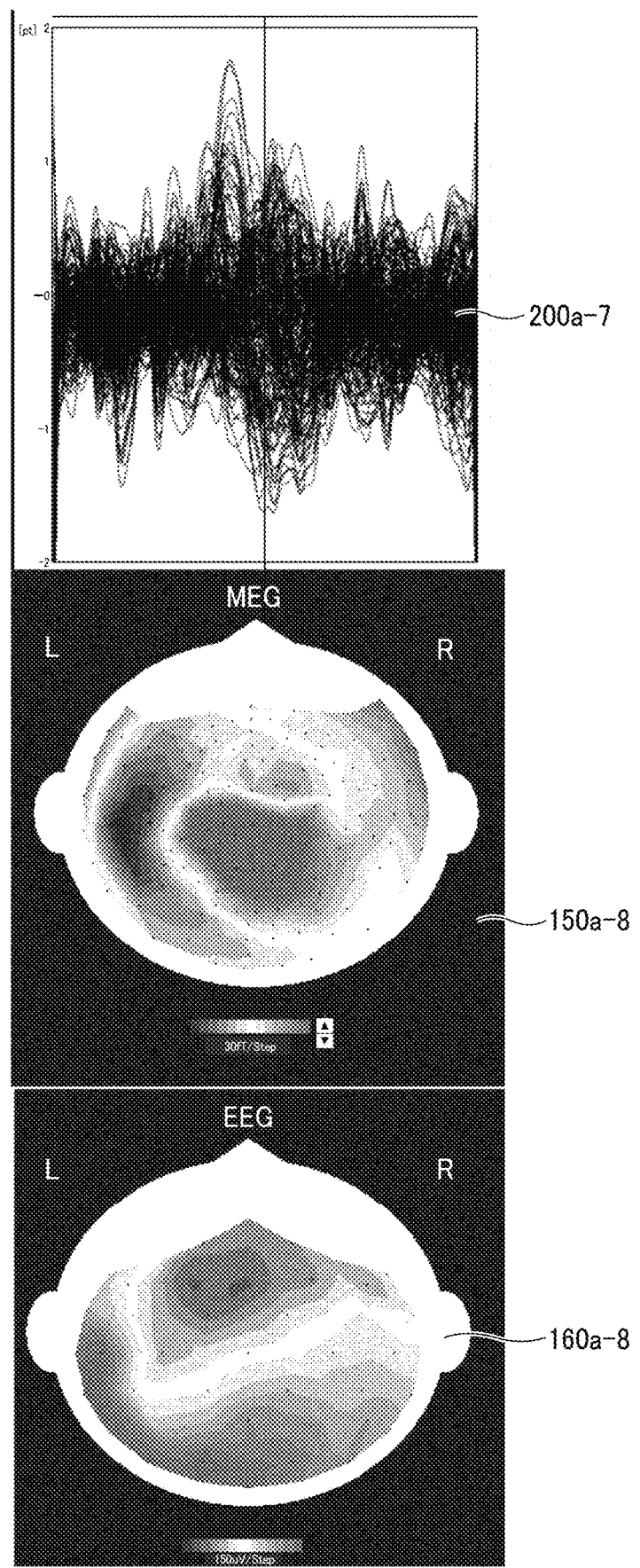
FIG. 30 is a diagram illustrating an alternative display displayed on an analyzing screen, according to an embodiment of the present disclosure.
Figure 31:
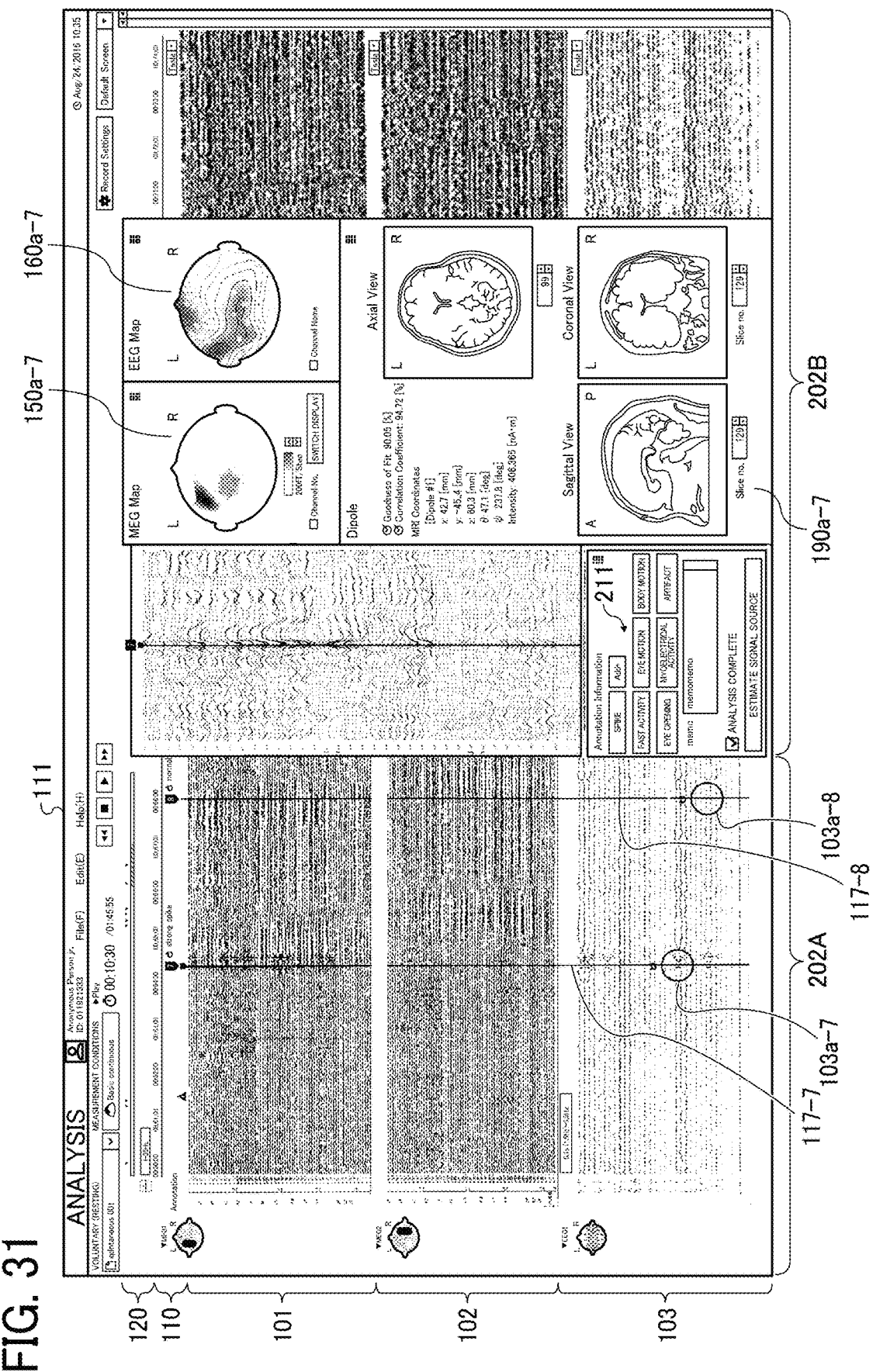
FIG. 31 is a diagram illustrating an alternative display displayed on an analyzing screen, according to an embodiment of the present disclosure.

Numerous additional modifications and variations are possible in light of the above teachings. It is therefore to be understood that within the scope of the appended claims, this disclosure may be practiced otherwise than as specifically described herein. For example, elements and/or features of different illustrative embodiments may be combined with each other and/or substituted for each other within the scope of this disclosure and appended claims. For example, some of the elements described in the above embodiments may be removed. Further, elements according to varying embodiments or modifications may be combined as appropriate. For example, the isomagnetic-field charts, equipotential maps, and the magnified display areas as illustrated in FIG. 20 and FIG. 22 may be all combined. In such a configuration, those items may be aligned in the time-axial direction of the waveform display areas 101 to 103. However, if priority is given to the browsability of waveform, those items may be aligned in the up-and-down directions as illustrated in FIG. 29 and FIG. 30. Alternatively, on the screen as illustrated in FIG. 21, magnified waveforms may be displayed side by side as illustrated in FIG. 31.

In the step S507 of FIG. 14, when waveforms near another annotation are selected after the isomagnetic-field chart 150a is displayed, the isomagnetic-field chart 150a that was being displayed is closed. However, no limitation is intended thereby. For example, the isomagnetic-field chart 150a may be closed when input data such as clicking with a mouse is received.

A program for the biomedical-signal measuring system 1 according to the above-described embodiment and variation may be installed for distribution in any desired computer-readable recording medium such as a compact disc, a read-only memory (CD-ROM), a flexible disk (FD), a compact disc-recordable (CD-R), and a digital versatile disk (DVD), a universal serial bus (USB) in a file format installable or executable by a computer, or may be provided or distributed via network such as Internet. Alternatively, various kinds of programs may be integrated in advance, for example, into a ROM inside the device for distribution.

APPENDICES

The disclosure of the present application involves the following aspects.

Appendix 1

As illustrated in FIG. 14, an information processing device comprises circuitry to: display, on a display device, a waveform display area indicating a waveform that indicates changes over time in a biomedical signal; and display a distribution display area indicating a distribution of the biomedical signal, wherein once input data indicating selection of a certain point of the waveform displayed in the waveform display areas is accepted (step S500) the distribution display area is displayed based on the input data (step S503) when the distribution display area is hidden from view, and the distribution indicated in the distribution display area before the input data is accepted is updated to a distribution based on the input data and is displayed (step S504) when the distribution display area is being displayed Appendix 2

As illustrated in FIG. 7, FIG. 14, and FIG. 15 In the information processing device according to Appendix 1 the distribution display area includes a first distribution display area (150; see FIG. 7) and a second distribution display area (150a-7; see FIG. 15), once input data indicating a certain point of the waveform displayed in the waveform display areas is accepted, the first distribution display area is hidden from view and the second distribution display area is displayed based on the input data (step S503 in FIG. 14) when the first display area is hidden from view, and the second distribution display area is hidden from view and the distribution indicated in the first distribution display area before the input data is accepted is updated to a distribution based on the input data and is displayed (step S504 in FIG. 14) when the first distribution display area is being displayed.

Appendix 3

(See FIG. 22 where an Isomagnetic-Field Chart and a Magnified View of Magneto-Encephalograph (MEG) Waveform are Displayed)
In the information processing device according to Appendix 2, when the second distribution display area is displayed, the circuitry further displays a second waveform display area in which a magnified view of the waveform at the certain point is displayed.

Appendix 4

(See FIG. 22 where an Isomagnetic-Field Chart and a Magneto-Encephalograph (MEG) Stack Waveform are Displayed)
In the information processing device according to Appendix 2, the waveform display area displays a plurality of waveforms arranged in parallel in up-and-down directions, and when the second distribution display area is displayed, the circuitry further displays a second waveform display area in which a plurality of waveforms at the certain point are superimposed on top of one another and displayed.

Appendix 5

(See FIG. 26 where, if a Magnified View of the Waveform on a Pop-Up Window is Double-Clicked, a Magnified View of the Waveform is Displayed as Illustrated in FIG. 8)
In the information processing device according to Appendix 3 or 4, once input data indicating selection of a certain point of the waveform displayed in the second waveform display areas is accepted (step S801), the circuitry closes the second distribution display area and the second waveform display area, and displays the first distribution display area and a magnified-waveform display area in which a magnified view of the waveform at the certain point is displayed (step S602).

Appendix 6

(See FIG. 15 and FIG. 17 where, after a Pop-Up Window Appears, the Pop-Up Window is Updated as a Different Point in Waveform is Selected)
In the information processing device according to Appendix 3 or 4, once input data indicating another point of the waveform displayed in the waveform display areas is accepted after the second distribution display area is displayed, the second distribution display area is updated and displayed.

Appendix 7

(See, for Example, FIG. 15 where a Pop-Up Window is Displayed on Waveforms Nearer a Point where a Point in Waveform is Selected than a Default Screen)
In the info, illation processing device according to Appendix 2, wherein the second distribution display area (150a-7) is displayed over the waveform in the waveform display area, and is displayed nearer the selected certain point of the waveform than a position at which the first distribution display area (150) is displayed.

Appendix 8

(See FIG. 24 where the Isomagnetic-Field Chart is Updated as the Timescale is Changed on a Pop-Up)
In the information processing device according to Appendix 3 or 4, an indicator (217a-7) indicating a certain point of the waveform displayed in the second waveform display area is displayed on the second waveform display area, and the second distribution display area is updated and displayed as the indicator is shifted in a time-axial direction of the waveform.

Appendix 9

(See FIG. 26 and FIG. 27 where the Isomagnetic-Field Chart is Displayed in a Different Manner when the Certain Point Selected in the Waveform is Near an Annotation)
In the information processing device according to Appendix 1, an annotation indicating a point of the waveform being displayed is displayable on the first waveform display area. When the certain point selected in the waveform includes the annotation ("YES" in the step S901 as in FIG. 27; "YES" in the step S1001 as in FIG. 28), the distribution display area is displayed based on the input data (step S904 or S1003) when the distribution display area is hidden from view, and the distribution indicated in the distribution display area before the input data is accepted is updated to a distribution based on the input data and is displayed (step S905 or S1009) when the distribution display area is being displayed. When the certain point selected in the waveform does not include the annotation ("NO" in the step S901 as in FIG. 27; "NO" in the step S1001 as in FIG. 28), the distribution display area is not displayed based on the input data ("YES" in the step S902, "NO" in the step S1001) when the distribution display area is hidden from view, and the distribution indicated in the distribution display area before the input data is accepted is updated to a distribution based on the input data and is displayed (step S905 or S1009) when the distribution display area is being displayed.

Appendix 10

(When a Point Near an Annotation is Single-Clicked, a Pop-Up Window is Displayed. When a Point Near the Annotation is Double-Clicked, the Screen Appears as in FIG. 8)

In the information processing device according to Appendix 2, an annotation indicating a point of the waveform being displayed is displayable on the first waveform display area, and when the distribution display area is hidden from view, the circuitry displays the second distribution display area (step S703 or S1003) when the accepted input data is first input data where a point in waveform including the annotation is selected ("YES" in the step S700 as in FIG. 25; "YES" in the step S1002 as in FIG. 28), and the circuitry displays the first distribution display area including a display area in which a magnified view of the waveform is displayed (step S707 or S1004) when the accepted input data is second input data where a point in waveform including the annotation is selected ("NO" in the step S700 as in FIG. 25; "NO" in the step S1002 as in FIG. 28).

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA), and conventional circuit components arranged to perform the recited functions.

What is claimed is:

1. An information processing device, comprising: circuitry configured to display, on a display device, a first waveform display area including a waveform that indicates changes over time in a biomedical signal; and wherein once input data indicating selection of a first point of the waveform displayed in the first waveform display area is accepted, the circuitry is further configured to display a distribution display area based on the input data when the distribution display area is hidden from view, update a distribution indicated in the distribution display area before the input data is accepted to a distribution based on the input data, and display the updated distribution when the distribution display area is being displayed.

2. An information processing device comprising:
circuitry configured to display, on a display device, a first waveform display area including a waveform that indicates changes over time in a biomedical signal;
wherein once input data indicating selection of a first point of the waveform displayed in the first waveform display area is accepted, the circuitry is further configured to
determine whether a first distribution display area is currently being displayed or is currently hidden from view,
in response to determining that the first distribution display area is currently hidden from view, display a second distribution display area based on the input data, and
in response to determining that the first distribution display area is currently being displayed, update a first distribution indicated in the first distribution display area before the input data is accepted to a second distribution based on the input data, and display the second distribution.

3. The information processing device according to claim 2, wherein the circuitry is further configured to display a plurality of waveforms arranged in parallel in up-and-down directions in the first waveform display area.

4. The information processing device according to claim 2, wherein the circuitry is further configured to display the second distribution display area over the waveform included in the first waveform display area, the second distribution display area being displayed near a line that indicates a time-position of the selected first point of the waveform than a position at which the first distribution display area is displayed.

5. The information processing device according to claim 2, wherein, the circuitry is further configured to display a magnified view of the waveform when a line that indicates a time-position of the first point is selected.

6. The information processing device according to claim 2, wherein after the display of the second distribution display area based on the input data and, in response to receiving additional input data indicating a selection of a second point of the waveform displayed in the first waveform display area, the circuitry is further configured to close the second distribution display area.

7. A computer-readable, non-transitory recording medium storing a program for causing a computer to execute a biomedical signal display method comprising:
displaying, on a first waveform display area, a waveform that indicates changes over time in a biomedical signal;
accepting input data indicating a certain point of the waveform selected in the first waveform display area;
displaying a distribution display area based on the input data when the distribution display area is hidden from view; and
updating the distribution indicated in the distribution display area before the input data is accepted to a distribution based on the input data and displaying the updated distribution when the distribution display area is being displayed.

8. A biomedical-signal measuring system, comprising: a measurement device to measure at least one biomedical signal of a test subject; a server to store the at least one biomedical signal measured by the measurement device; and an information processing device to analyze the at least one biomedical signal stored on the server, the information processing device comprising a display device; and circuitry configured to display, on the display device, a first waveform display area including a waveform that indicates changes over time in a biomedical signal, and wherein, once input data indicating selection of a certain point of the waveform displayed in the first waveform display area is accepted, the circuitry is further configured to cause the display device to display a distribution display area based on the input data when the distribution display area is hidden from view, and update a first distribution indicated in the distribution display area before the input data is accepted to a second distribution based on the input data, and display the second distribution when the distribution display area is being displayed.

* * * * *